United States Patent
Nozato

(10) Patent No.: US 10,213,106 B2
(45) Date of Patent: Feb. 26, 2019

(54) SYSTEM AND METHOD FOR EYE TRACKING DURING RETINAL IMAGING

(71) Applicant: CANON KABUSHIKI KAISHA, Tokyo (JP)

(72) Inventor: Koji Nozato, Yokohama-shi (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/722,784

(22) Filed: Oct. 2, 2017

(65) Prior Publication Data
US 2018/0020915 A1    Jan. 25, 2018

Related U.S. Application Data

(63) Continuation of application No. 15/201,182, filed on Jul. 1, 2016, now Pat. No. 9,795,294.

(51) Int. Cl.
| | |
|---|---|
| A61B 3/15 | (2006.01) |
| A61B 3/10 | (2006.01) |
| A61B 3/00 | (2006.01) |
| A61B 3/113 | (2006.01) |
| A61B 3/12 | (2006.01) |

(52) U.S. Cl.
CPC ............ *A61B 3/152* (2013.01); *A61B 3/0025* (2013.01); *A61B 3/1025* (2013.01); *A61B 3/113* (2013.01); *A61B 3/1225* (2013.01)

(58) Field of Classification Search
CPC .......... A61B 3/152; A61B 3/14; A61B 3/102; A61B 3/12; A61B 3/0025
USPC ............................................ 351/200–246
See application file for complete search history.

(56) References Cited

U.S. PATENT DOCUMENTS

| | | | | |
|---|---|---|---|---|
| 5,568,208 A * | 10/1996 | Van de Velde | ...... | A61B 3/1025 351/205 |
| 6,186,628 B1 * | 2/2001 | Van de Velde | ......... | A61F 9/008 351/205 |
| 9,033,500 B2 * | 5/2015 | Utsunomiya | .......... | A61B 3/102 351/206 |

* cited by examiner

*Primary Examiner* — Mohammed A Hasan
(74) *Attorney, Agent, or Firm* — Canon U.S.A., Inc. IP Division

(57) ABSTRACT

A method, a, controller, a non-transitory computer readable storage medium encoded with instructions; each of which control an apparatus to produce multiple images of an area of an eye in parallel. Selecting one of the images for estimating a change in position of the area to be used for tracking the area of the eye being imaged.

19 Claims, 19 Drawing Sheets

SYSTEM AND METHOD FOR EYE TRACKING DURING RETINAL IMAGING

CROSS REFERENCE TO RELATED APPLICATION

This application is a continuation, and claims the benefit, of U.S. patent application Ser. No. 15/201,182 filed Jul. 1, 2016 (now U.S. Pat. No. 9,795,294 B1). U.S. patent application Ser. No. 15/201,182 is hereby incorporated by reference herein in its entirety.

BACKGROUND

Field of Art

The present disclosure relates to an ophthalmic apparatus, a system and a method for controlling an ophthalmic apparatus.

Description of the Related Art

An ophthalmoscope is an apparatus for gathering information about the interior portion of an eye (fundus). A simple direct view ophthalmoscope is a handheld device used by an optician to directly view the fundus which may include a light source, an aperture, and one or more lenses. An electronic ophthalmoscope uses one or more sensors to obtain fundus images. These fundus images are then displayed to the optician with a display device. High resolution ophthalmoscope may use lasers to obtain high resolution fundus images. High resolution ophthalmoscope may also include adaptive optics to obtain even higher resolution fundus images. The adaptive optics can be used to compensate for the static and dynamic distortions introduced by the eye being examined. Examples of ophthalmoscopes include: ophthalmic image pickup apparatuses; fundus imaging systems; scanning laser ophthalmoscopes (SLO); adaptive optics scanning laser ophthalmoscope (AO-SLO); optical coherence tomographs (OCT); that utilize the interference of low coherence light; adaptive optics optical coherence tomographs (AO-OCT); etc. These ophthalmoscopes are important tools for the study of the human fundus in both normal and diseased eyes.

In AO-SLO and AO-OCT the adaptive optics (AO) are an optical correction system that measures the aberration of the eye and corrects for the measured aberration. The AO-SLO and AO-OCT may measure the wavefront of the eye using a Shack-Hartmann wavefront sensor system. A deformable mirror or a spatial-phase modulator is then driven to correct for the measured wavefront, and an image of the fundus is acquired, thus allowing AO-SLO and AO-OCT to acquire high-resolution images.

Eye movement is a big issue for imaging using these systems. A SLO may take multiple images for averaging and constructing panoramic images. In order to properly construct these images, each image should be in an exact position. This can be difficult because the eye moves continuously during imaging. Especially, on small FOV (Field Of View) systems such as AO-SLO eye movement can be quite large relative to the frame size. Sometimes the imaging area can go out of frame due solely to the eye movement.

In order to address this problem, eye position tracking systems are used. An eye position tracking system estimates an eye position using a position detection apparatus and shifts the imaging area according to the estimated eye movement using one or more tracking mirrors or by adjusting the scanning mirrors. The position detection apparatus may use image based position calculation methods that include detecting specific features or by analysis of the image as a whole.

There are a plurality of imaging techniques that may be used to image the eye using an AO-SLO or an AO-OCT. These include, confocal imaging, dark field imaging, fluorescence imaging, multispectral imaging, non-confocal imaging, split detection imaging, etc. An imaging apparatus may be designed to use multiple imaging techniques simultaneously. While this provides more information for diagnosis and investigation, it also present challenges for an image based tracking system. The plurality of images can produce conflicting tracking information.

What is needed is an apparatus and method of handling image based eye tracking with multiple sometimes conflicting tracking information.

SUMMARY

Embodiments are a method, a, controller, a non-transitory computer readable storage medium encoded with instructions; each of which may control a scanning light measurement apparatus to produce images of an area of an eye. The apparatus may scan light across the area. The apparatus may collect light from the eye. The apparatus may divide the light collected from the eye into a first portion of light and a second portion of light. The apparatus may generate first detection data that is representative of the first portion of the collected light. The apparatus may generate second detection data that is representative of the second portion of collect light.

In an embodiment the method may comprise receiving the first detection data and the second detection data. The method may also comprise constructing a first image based on the first detection data from a first area of the eye obtained by the apparatus during a first period of time. A length of time of the first period of time is a time for one scan of the first area. The method may also comprise constructing a second image based on the second detection data from the first area of the eye obtained by the apparatus during the first period of time. The method may also comprise selecting the first image or the second image as a position detection image. The method may also comprise estimating a change in position of the first area during the first period of time based on the position detection image. The method may also comprise sending instructions to the apparatus to adjust an imaging area based on the estimated change in position of the first area.

In an embodiment, the first portion of the collected light may have a first range of wavelengths. In an embodiment, the second portion of the collected light may have a second range of wavelengths. In an embodiment, the first range of wavelengths may be different from the second range of wavelengths.

In an embodiment, the first portion of the collected light may be fluorescence light. In an embodiment, the second portion of the collected light may not be fluorescence light.

In an embodiment, the first portion of the collected light does not pass through a confocal pinhole before being detected by a first detector to generate first detection data. In an embodiment, the second portion of the collected light passes through a first confocal pinhole before being detected by a second detector to generate second detection data.

In an embodiment, selecting the first image or the second image as the position detection image may comprise: estimating a first cross correlation value based on the first image and a previous first image; estimating a second cross correlation value based on the second image and a previous second image; selecting the first image as the position detection image if the first cross correlation is greater than second cross correlation image; and selecting the second image as the position detection image if the second cross correlation is greater than first cross correlation image.

In an embodiment, selecting the first image or the second image as the position detection image may comprise: selecting the first image as the position detection image if the average signal strength of the first image is greater than average signal strength of the second image; and selecting the second image as the position detection image if the average signal strength of the second image is greater than average signal strength of the first image.

In an embodiment, selecting the first image or the second image as the position detection image may comprise: estimating a first difference based on a difference between a focus position of the first image relative to a set focus position; estimating a second difference based on a difference between a focus position of the second image relative to the set focus position; and selecting the first image as the position detection image if the first difference is less than second difference.

In an embodiment, the position detection image is set as a reference image which is used as a point of comparison for image tracking in subsequent position tracking during a second period of time after the first period of time.

In an embodiment, the reference image may be replaced with a reference new image.

In an embodiment, replacing the reference image with the new reference image may comprise: selecting the new reference image from a plurality of images.

In an embodiment, the new reference image may be selected based on the average intensity of each of the plurality of images.

In an embodiment, the new reference image may be selected based on a distribution of intensity of pixels within each of the plurality of images.

In an embodiment, the new reference image may be selected based on cross correlation coefficients calculated among the plurality of images.

In an embodiment, the new reference image may be constructed from an average of a plurality of images.

An embodiment may be a controller configured to control a scanning light measurement apparatus to produce images of an area of an eye. The apparatus may scan light across the area. The apparatus may collect light from the eye. The apparatus may divide the light collected from the eye into a first portion of light and a second portion of light. The apparatus may generate first detection data that is representative of the first portion of the collected light. The apparatus may generate second detection data that is representative of the second portion of collect light.

The controller may comprise: a processor; and a memory. The processor may receive the first detection data and the second detection data. The processor may construct a first image based on the first detection data from a first area of the eye obtained by the apparatus during a first period of time. A length of time of the first period of time is a time for one scan of the first area. The processor may construct a second image based on the second detection data from the first area of the eye obtained by the apparatus during the first period of time. The processor may select the first image or the second image as a position detection image. The processor may estimate a change in position of the first area during the first period of time based on the position detection image.

The processor may send instructions to the apparatus to adjust an imaging area based on the estimated change in position of the first area.

An embodiment may be a controller that further comprises the light measurement apparatus controlled by the controller.

In an embodiment the light measurement apparatus may further comprise one or more light sources to provide the light that is scanned across the area; and a scanner for scanning the light across the area.

An embodiment may be a non-transitory computer readable storage medium encoded with instructions for performing a method of controlling a scanning light measurement apparatus to produce images of an area of an eye. The apparatus may scan light across the area. The apparatus may collect light from the eye. The apparatus may divide the light collected from the eye into a first portion of light and a second portion of light. The apparatus may generate first detection data that is representative of the first portion of the collected light. The apparatus may generate second detection data that is representative of the second portion of collect light.

An embodiment may include instructions for receiving the first detection data and the second detection data. An embodiment may include instructions for constructing a first image based on the first detection data from a first area of the eye obtained by the apparatus during a first period of time, wherein a length of time of the first period of time is a time for one scan of the first area. An embodiment may include instructions for constructing a second image based on the second detection data from the first area of the eye obtained by the apparatus during the first period of time. An embodiment may include instructions for selecting the first image or the second image as a position detection image. An embodiment may include instructions for estimating a change in position of the first area during the first period of time based on the position detection image. An embodiment may include instructions for sending instructions to the apparatus to adjust an imaging area based on the estimated change in position of the first area.

BRIEF DESCRIPTION OF THE DRAWINGS

The accompanying drawings, which are incorporated in and constitute a part of the specification, illustrate exemplary embodiments.

DESCRIPTION OF THE EMBODIMENTS

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an image photographing apparatus as disclosed in the following which is used to inspect an eye as described below may also be used to inspect other objects including but not limited to skin, and internal organs.

Ophthalmoscope I

Figure 1A:
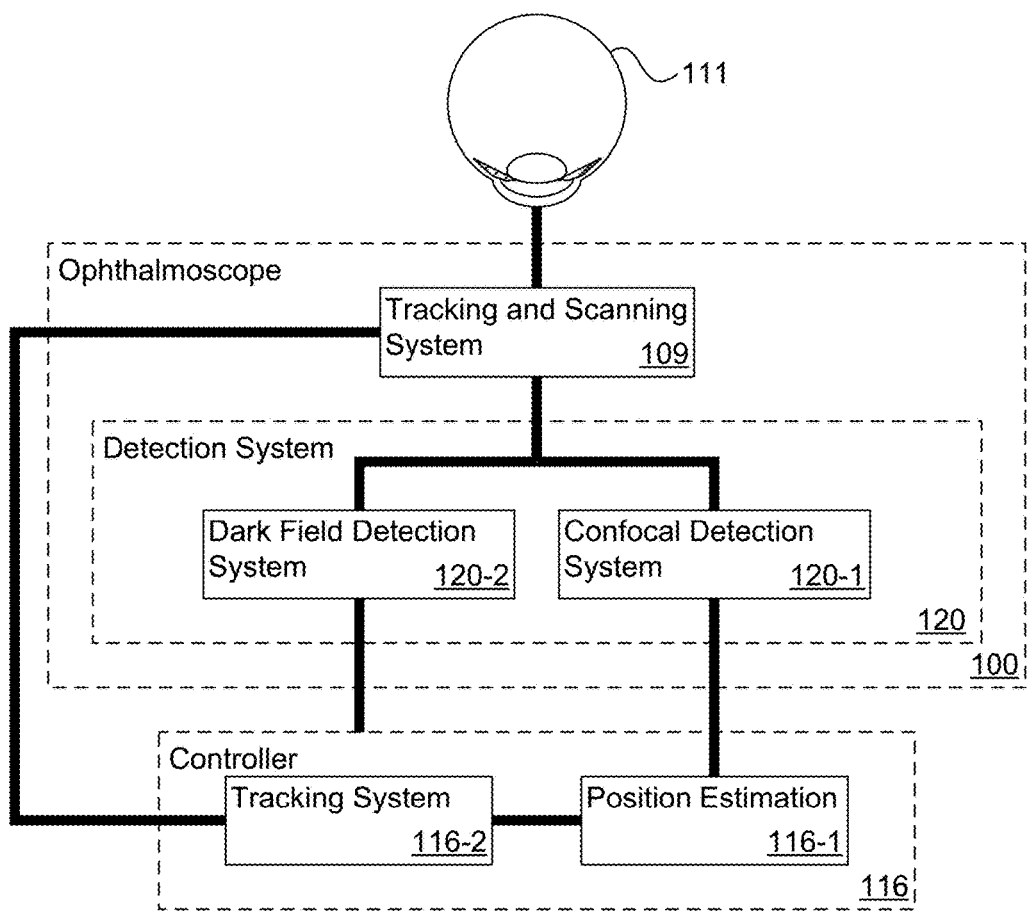
FIG. 1A is a block diagram of an apparatus in which an embodiment may be implemented.

FIG. 1A is a block diagram in which an embodiment, such as an ophthalmoscope 100 may be implemented. The ophthalmoscope 100 is used to image a subject 111 such as an eye and includes a tracking and scanning system 109. The tracking and scanning system 109 may be implemented as a single tip-tilt mirror that does both tracking and scanning. The tracking and scanning system 109 may include a scanning system 109-1 and a tracking system 109-2. The scanning system 109-1 may implemented as a single tip-tilt mirror or as a first axis scanning mirror 109-3 and a second axis scanning mirror 109-4. The first axis is substantially orthogonal to the second axis. Substantially in the context of the present disclosure means within the alignment and measurement tolerances of the system The first axis scanning mirror 109-3 may be resonant scanner. The resonant scanner may be driven by a sine wave or some other periodic signal. The second axis scanner 109-4 may be a servo scanner that is driven by a triangle signal, a pyramid signal, or a sawtooth signal. The scanners may be driven by an electric motor, a piezoelectric actuator, a magnetostrictive actuator, and/or may be a mems system. The tracking system 109-2 may be a tip-tilt mirror or a set of two stepping mirrors. One or more of the mirrors may be used simultaneously for both tracking and scanning. The tracking and scanning system 109 may also use other methods besides rotating mirrors for steering optical beams such as acousto-optic deflectors, electro-optic deflectors, wavefront phase steering, and other well-known techniques. The tracking and scanning system may include one or more optical components (such as mirrors, aperture, and/or lenses) for transmitting a measurement beam and return light between the various steering components. The various optical components that do the beam scanning and tracking may be in a conjugate optical relationship with each other. The tracking and scanning optical system 109 may include one or more additional scanners.

A scanning period of the first axis scanner 109-3 is less than the scanning period of the second axis scanner 109-4. The order of the first axis scanner 109-3 and the second axis scanner 10942 may be exchanged without impacting the operation of an exemplary embodiment.

The ophthalmoscope 100 may include a detection system 120. The detection system 120 may include a first detection system 120-1 and a second detection system 120-2. The first detection system may be a confocal detection system such as illustrated in FIG. 1A. The second detection system 120-2 may be a dark field detection system such as the system illustrated in FIG. 1A. The detection system 120 may include other types of detection systems besides confocal detection system and dark field detection system such as a fluorescence detection system, a non-confocal detection system, a split detection system, a multi-wavelength detection system, etc.

The ophthalmoscope 100 may send data such as images, or data that is converted into images by the controller 116 from each of the detection systems to the controller 116. The controller 116 may take the data from the first detection system 120-1 and use that information to estimate how the subject 111 has moved during the imaging process with an image based position estimation system 116-1. The image based position estimation system 116-1 may be implemented using the processor 124 and the memory 126 of the controller 116, and may also make use of the PC 117 and the GPU 128 which may implement a series of instructions that may include performing operations on images obtained by the detection system 120 with reference image also obtained by the detection system 120. The controller 116 may then take the estimated position from the first detection system 120-1 and feed that into a tracking system 116-2. The tracking system 116-2 may be implemented using the processor 124 and the memory 126 of the controller 116, and may also make use of the PC 117 and the GPU 128 which may implement a series of instructions that include performing calculations based on the current positions of the tracking and scanning system 109, past positions of the tracking and scanning system, lag time of the tracking and scanning system 109, and the results of the estimated position. The tracking system 116-2 may use known feedback control techniques to calculate new control signals for the tracking and scanning system 109. The controller 116 may then send the new control signals to the ophthalmoscope 100. The ophthalmoscope 100 may then receive the new control signals and use that information to re-position the tracking system.

Tracking mirror(s) are thus controlled with only position information calculated from the images from one of the detection systems (e.g. confocal). For example, confocal images are used for position detection at all times during imaging session. Confocal images from the confocal detection system 120-1 are sent to the image based image position estimation system 116-1 of the controller 116. Then the calculated position information is sent to the tracking system 116-2 of the controller 116. The tracking system 116-2 controls the tracking and scanning system 109 according to the position information. This embodiment allows a single tracking system to be used while multiple detection systems gather information about the subject. A disadvantage of this system is that optimum tracking information is not always used to obtain quality images from all of the detection systems, and the tracking system does not take full advantage of all of the information that is available.

Controller

Figure 1B:
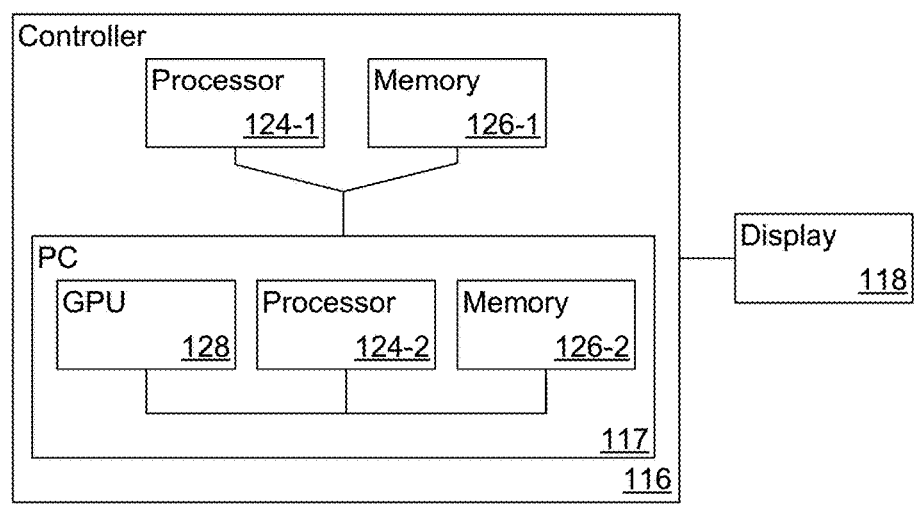
FIG. 1B is an illustration of a controller in which an embodiment may be implemented.

FIG. 1B is an illustration of the controller 116 that may be used in an embodiment. The controller 116 may also include a PC 117. The controller 116 receives input values and outputs control values. The controller 116 may be a general purpose computer, a device specifically designed to control the ophthalmoscope or measuring instrument, or a hybrid device that uses some custom electronics along with a general purpose computer (PC) 117. The input values and control values may be digital values or analog values. The controller 116 may include an analog to digital converter (ADC) and a digital to analog converter (DAC). The input values may include one more values such as a signal from the wavefront sensor 115, a signal from the detector 114, and one or more values from one or more other sensors. The control values may include control values sent to a wavefront adjustment device 108 and values sent to one or more of the scanners 109-1, 109-2, and 109-3. The control values may include additional values to other components of the instrument.

The controller 116 includes a processor 124-1. The processor 124-1 may be a microprocessor, a CPU, an ASIC, a DSP, and/or a FPGA. The processor 124-1 may refer to one or more processors that act together to obtain a desired result. The controller 116 may include a memory 126-1. The memory 226-1 may store calibration information. The memory 226-1 may also store software for controlling the ophthalmoscope. The memory 226-1 may take the form of a non-transitory computer readable storage medium. The non-transitory computer readable storage medium may include, for example, one or more of a hard disk, a random-access memory (RAM), a read only memory (ROM), a distributed storage system, an optical disk (CD, DVD or Blu-Ray Disc, a flash memory device, a memory card, or the like. The controller 116 may include input devices such as a keyboard, a mouse, a touch screen, knobs, switches, and/or buttons.

The controller 116 may be connected to a computer (PC) 117 via a direct connection, a bus, or via a network. The computer 117 may include input devices such as a keyboard, a mouse, and/or a touch screen. The computer 117 may be connected to a display 118. The results and/or data produced by the ophthalmoscope 100 may be presented to a user via the display 118. The PC may include a processor 124-2, a memory 126-2. The PC 117 may also include one or more GPUs 128.

Ophthalmoscope II

Figure 1C:
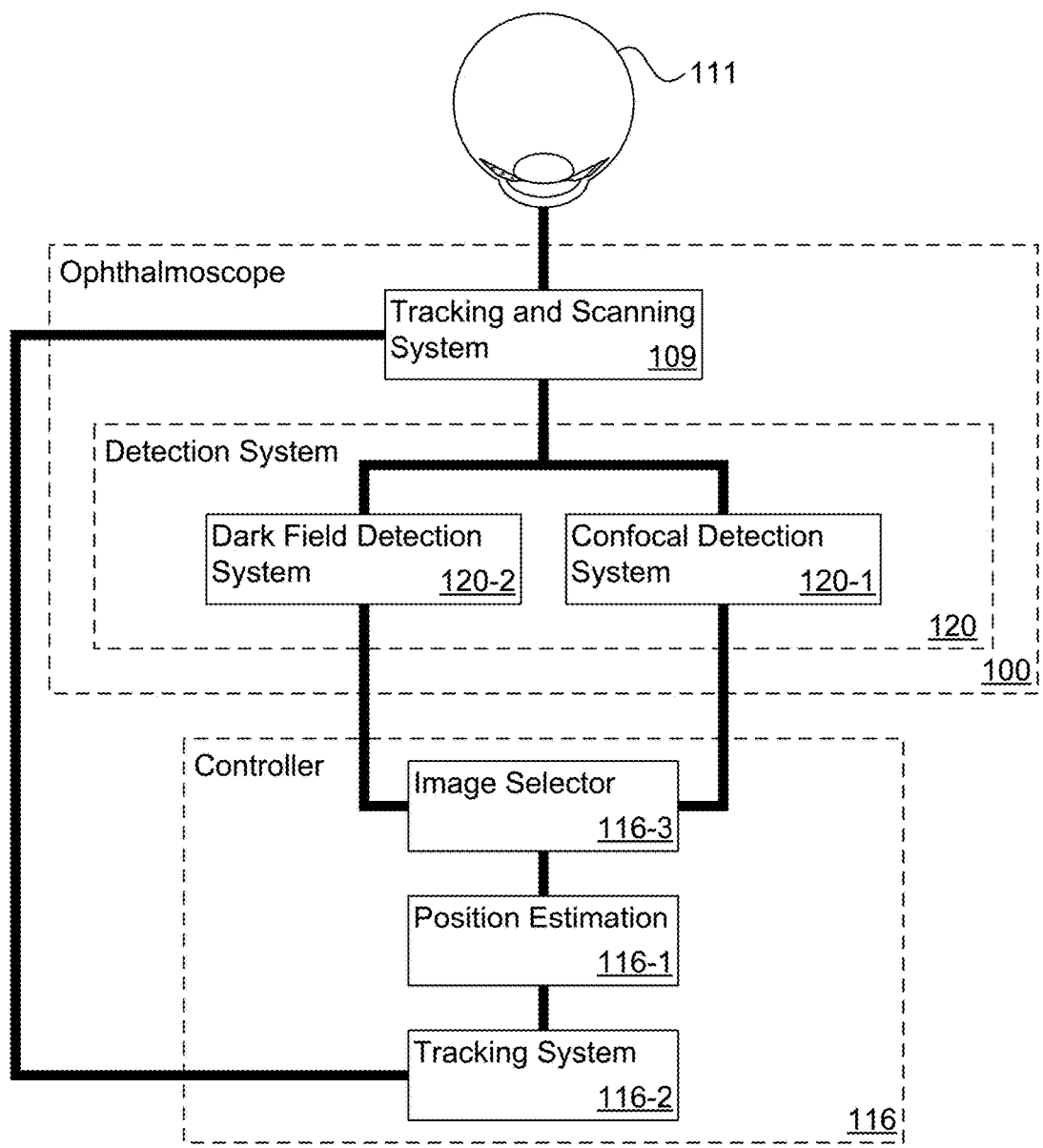
FIG. 1C is a block diagram of an apparatus in which an embodiment may be implemented.

FIG. 1C is an illustration another embodiment in which the controller 116 takes into account information from both detection systems. As in FIG. 1A the ophthalmoscope 100 includes a detection system 120. The detection system 120 includes multiple detection systems including a first detection system 120-1 and a second detection system 120-2. In one example the first detection system 120-1 is a confocal detection system and the second detection system 120-2. Both detection systems use a common scanning and tracking system 109. The ophthalmoscope 100 sends data from both the first detection system 120-1 and the second detection system 120-2 to the controller 116.

The controller 116 receives the data from both the first detection system 120-1 and the second detection system 120-2. The data from the detection systems may be analog data, digital data, structured data, images, and/or raw data which the controller 116 converts images. The controller 116 will use an image selection system 116-3 to select which of the images from each of the detectors are used for tracking. The controller 116 may then take the selected data and use that information to estimate how the subject 111 has moved during the imaging process with an image based position estimation system such as 116-1. The controller 116 may then take the estimated position from the selected detection system and feed that into a tracking system 116-2. The tracking system 116-2 may use known feedback control techniques to calculate new control signals for the tracking and scanning system 109 based on the selected data. The controller 116 may then send the new control signals to the ophthalmoscope 100 based on the selected data. The ophthalmoscope 100 may then receive the new control signals and use that information to re-position the tracking system.

In an exemplary system, the first detection system 120-1 is a confocal detection system and the second detection system is a dark field detection system. During an imaging session, both a confocal image and a dark field image are acquired simultaneously. Then these images are sent to the image selector 116-3. The image selector 116-3 decides which image is better for calculating the imaging position. Then the selected image is sent to the image based position estimation system 116-1. The image based position estimation system 116-1 estimates the position of the subject. Then the estimated position information is sent to the tracking system 116-2. The tracking system 116-2 controls the tracking and scanning system 109 according to the position information.

Ophthalmoscope III

Figure 1D:
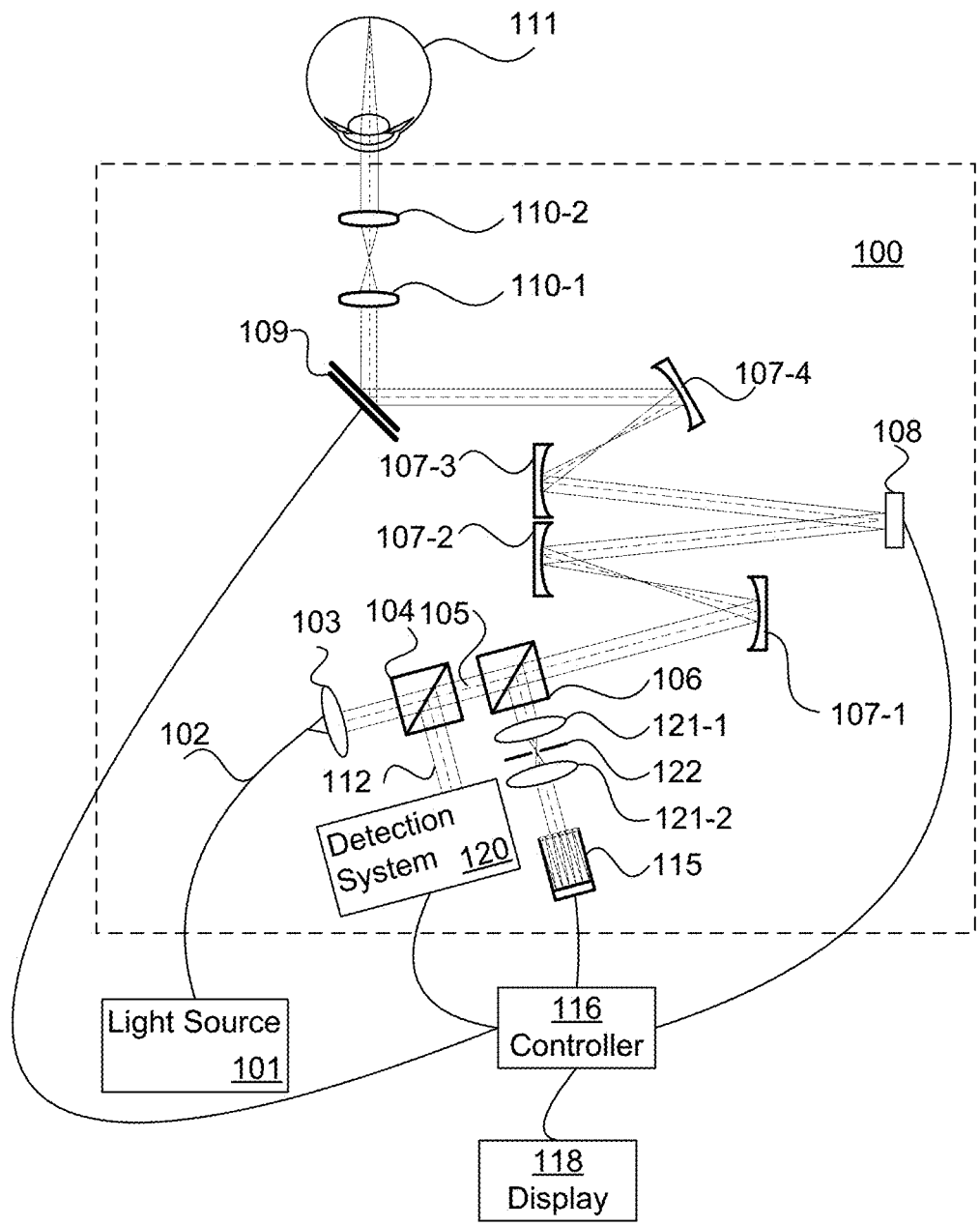
FIG. 1D is a generalized illustration of an apparatus in which an embodiment may be implemented.

An embodiment is described with reference to an ophthalmoscope 100 such as the fundus image photographing apparatus illustrated in FIG. 1D. Embodiments are directed towards systems, methods, non-transitory computer readable medium, and software which are used in connection with an imaging system such as an ophthalmoscope 100. FIG. 1D is an illustration of an exemplary ophthalmoscope 100. An ophthalmoscope 100 is a system or apparatus for obtaining information about an interior portion of the subject 111 (e.g., the fundus or retina).

An exemplary embodiment may be a scanning ophthalmoscope. A scanning ophthalmoscope scans a spot across the subject 111 with the tracker and scanner 109. The spot may be a spot of light from a light source 101 that is scanned across the subject 111.

In an exemplary embodiment 100, the spot of light is produced by the light source 101. The light source 101 may be incorporated into the ophthalmoscope 100; alternatively, the ophthalmoscope 100 may include an input for receiving the light source 101. The input for the light source 101 may be a fiber optic input 102 or a free space input (not shown). The fiber optic input 102 may be a single mode optical fiber, a multi-mode optical fiber, a polarization maintaining optical fiber, an optical fiber bundle, or some other wave guide type input. The light source 101 may be a laser, a broadband light source, or multiple light sources. In an exemplary embodiment, the light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare perceived by the subject being inspected and to maintain imaging resolution.

In an exemplary embodiment, light emitted from the light source 101 passes through a single-mode optical fiber 102, and is radiated as collimated light (measuring light 105) by a collimator 103.

In an exemplary embodiment, the polarization of the irradiated light may be adjusted by a polarization adjusting member 119 (not shown) provided in a path of the single-mode optical fiber 102. In an alternative configuration, the light source 101 is polarized and the single-mode optical fiber 102 is polarization maintaining fiber. In another configuration, the polarization adjusting member may be placed after the collimator 103. Alternatively, the polarization adjusting member may be replaced with a polarizer. In an alternative embodiment, the irradiated light may be unpolarized, depolarized, or the polarization may be uncontrolled.

The measuring light 105 radiated from the collimator 103 passes through a light division portion 104 including a beam splitter. An exemplary embodiment includes an adaptive optical system.

The adaptive optical system may include a light division portion 106, a wavefront sensor 115, wavefront adjustment device 108, and reflective mirrors 107-1, 107-2, 107-3, and 107-4 for guiding the measuring light 105 to and from those components. The reflective mirrors 107-1 to 107-4 are provided to guide the measuring light 105 to and from the pupil of the subject 111, the wavefront sensor 115, and the wavefront adjustment device 108. The reflective mirrors may be replaced with suitable optics, such as lenses and/or apertures. Likewise, the lenses may be replaced with mirrors. The wavefront sensor 115 and the wavefront adjustment device 108 may be in an optically conjugate relationship. A beam splitter may be used as the light division portion 106. The wavefront sensor 115 may be a Shack-Hartmann sensor or other type of sensor that gathers information that is representative on the spatial nature of the wavefront of light coming from the subject. Other examples of types of sensors that provide information about the shape of a wavefront include but are not limited to: a pyramid wavefront sensor; a common path interferometer; a Foucault knife-edge tester; a multilateral shearing interferometer; a Ronchi tester; and a Shearing Interferometer.

The measuring light 105 passing through the light division portion 106 is reflected by the reflective mirrors 107-1 and 107-2 so as to enter the wavefront adjustment device 108. The measuring light 105 is reflected by the wavefront adjustment device 108 and is further reflected by the reflective mirrors 107-3 and 107-4.

The wavefront adjustment device 108 may be a transmissive device or a reflective device. The wavefront adjustment device 108 may be an addressable spatial light phase modulator that allows relative phases across a beam coming into the wavefront adjustment device 108 to be adjusted such that relative phases across the beam coming out of the wavefront adjustment device 108 are adjustable. In an exemplary embodiment, one or two spatial phase modulators each including a liquid crystal element is used as the wavefront adjustment device 108. The liquid crystal element may modulate a phase of only a specific polarized component. In which case, two liquid crystal elements may be employed to modulate substantially orthogonal polarized components of the measuring light 105. In an alternative embodiment, the wavefront adjustment device 108 is a deformable mirror.

The measuring light 105 reflected off mirror 107-4 is two-dimensionally scanned by a scanning optical system 109. The tracking and scanning system 109 was described above in other embodiment and is substantially the same in this embodiment The measuring light 105 scanned by the tracking and scanning optical system 109 is radiated onto the subject 111 through eyepieces 110-1 and 110-2. The measuring light radiated to the subject 111 is reflected, scattered, or absorbed by the fundus 111. When the eyepieces 110-1 and 110-2 are adjusted in position, suitable irradiation may be performed in accordance with the diopter prescription of the subject 111. Lenses may be used for the eyepiece portion in this embodiment, but other optical components such as spherical mirrors may also be used.

Light which is produced by reflection, fluorescence, and/or scattering by a fundus of the subject 111 then travels in the reverse direction along the same path as the incident measurement light. A part of the reflected light is reflected by the light division portion 106 through a first lens 121-1 through a pinhole 122 and through a second lens 121-2 to the wavefront sensor 115 to be used for measuring a light beam wavefront. The first and second lenses 121 may be replaced with curved mirrors.

In an exemplary embodiment, a Shack-Hartmann sensor is used as the wavefront sensor 115. However, an exemplary embodiment is not limited to a Shack-Hartmann sensor. Another wavefront measurement unit, for example, a curvature sensor may be employed. The wavefront sensor 115 and/or the controller 116 may make use of a method of obtaining the wavefront by reverse calculation from the spot images.

In FIG. 1D, when the reflected light passes through the light division portion 106, a part thereof is reflected on the light division portion 104 and is guided to a detection system 120 that provides digital and/or analog signals which are connected to the controller 116 as collimated measurement light 112. The digital and/or analog signals represent information about the subject 111 as detected by the detection system 120. The digital and/or analog signals are processed by the controller 116 or other suitable processing device into an image of the subject 111 and the image is displayed on a display 118.

The wavefront sensor 115 is also connected to the controller 116. The received wavefront is transferred to the controller 116. The wavefront adjustment device 108 is also connected to the controller 116 and performs modulation as instructed by the controller 116. The controller 116 calculates a modulation amount (correction amount) to obtain a wavefront having less aberration based on the wavefront obtained by a measuring result of the wavefront sensor 115, and instructs the wavefront adjustment device 108 to perform the modulation according to the modulation amount. The wavefront measurement and the instruction to the wavefront adjustment device are repeated and a feedback control loop is maintained so as to obtain a suitable wavefront for obtaining an image by the detection system 120.

In an exemplary embodiment, the light division portions 104 and 106 are partially reflective mirrors. In an alternative exemplary embodiment, the light division portions 104 and/or 106 may include fused fiber couplers. In another alternative exemplary embodiment, the light division portions 104 and/or 106 may include dichroic reflectors, in which case a different wavelength of light is used for obtaining an image of the fundus then is used for detecting the spatial phase image that controls the adaptive optics system.

The detection system 120 may detect scattering, reflection, or fluorescence associated with the scanning spot. The detection system may make use of confocal microscopy techniques in which an aperture associated with the scanning spot is used to increase the resolution and/or contrast of the detection system.

The adaptive optics system described above includes at least the wavefront sensor 115 and the wavefront adjustment device 108 so that the aberration of the subject's eyes can be measured and compensated for. A deformable mirror (DM)

or a spatial light phase modulator (SLM) can be used as the wavefront adjustment device 108. Since the typical SLM has a large number of actuators, it can modulate a wavefront more precisely than a DM can. A liquid crystal on silicon spatial light modulator (LCOS-SLM) may be used as the wavefront adjustment device 108. The LCOS-SLM 108 can be controlled to provide a precise spatial modulation of the phase of the beam that is used to illuminate the subject.

Detection System

Figure 1E:
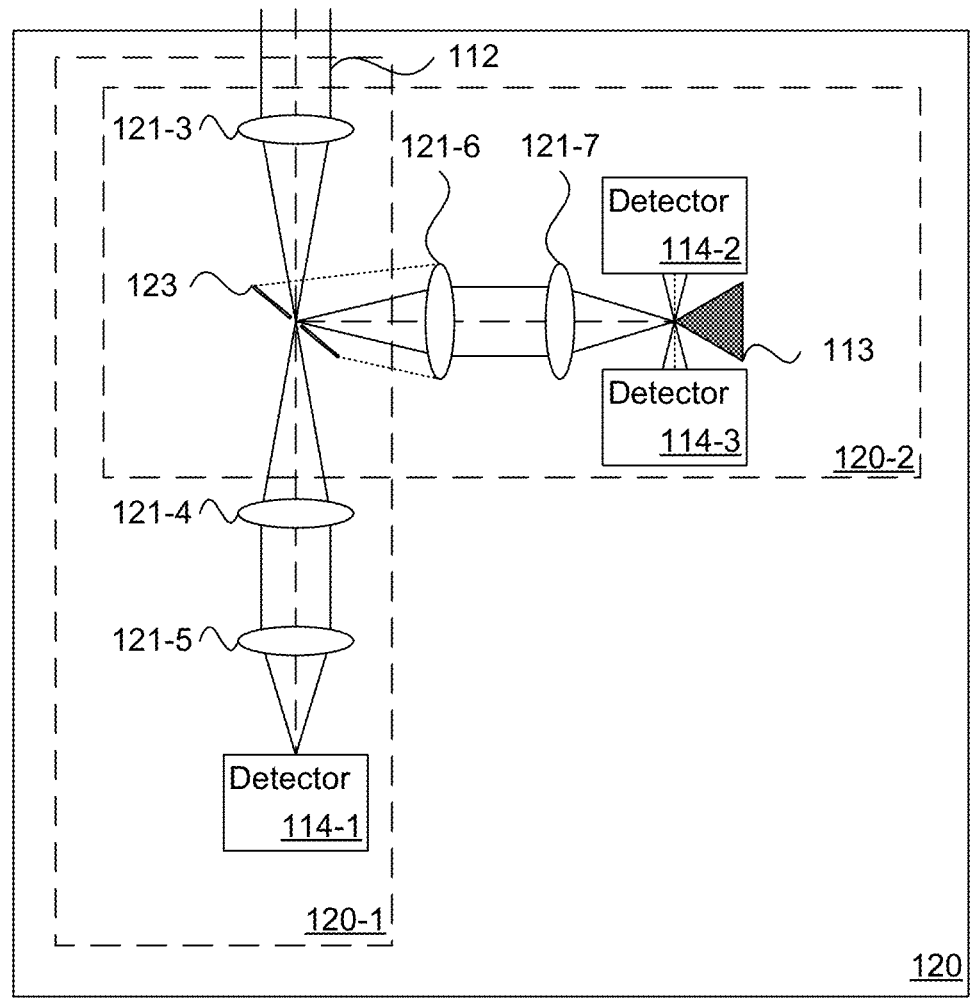
FIG. 1E is a generalized illustration of a detection system as may be used in an embodiment.

FIG. 1E is an illustration of an exemplary detection system 120 as used in an embodiment. The detection system 120 may receive collimated measurement light 112 from the subject 111 as split off by the light division portion 104. The detection system 120 may include a spatial light splitter 123. The spatial light splitter 123 may be an annular mirror. An annular mirror is a ring shaped mirror that includes an inner light transmitting portion and an outer ring reflecting portion. The annular mirror may be positioned at an angle such as 45° relative to the collimated light from the subject 111 as received by the detection system 120. The inner portion of the spatial light filter 123 may have an elliptical shape to compensate for the tilt of the annular mirror. The inner diameter of the inner light transmitting portion may have a diameter on the order of 1 airy disc diameter (ADD) of the measurement light. In one embodiment, the diameter of the inner light transmitting is adjustable such as by switching components or with adjustable components. The collimated measurement light 112 may be focused onto the inner portion of the spatial light filter 123 by a third lens 121-3. Light that passes through the spatial light filter 123 may be collected by a fourth lens 121-4 and collimated. A fifth lens 121-5 may receive the collimated light and focus it onto a detector 114-1. The first detection system may be formed from the components 123, 121-3, 121-4, 121-5, and 114-1 which together form a confocal measurement system. In one embodiment, one or more of the lenses 121 may be replaced with curved mirrors. In one embodiment, the collimated measurement light 112 is not completely collimated or the collimation varies and the lens 121-3 is adjusted or changed to compensate for the state of the collimation such that the light is focused onto the inner portion of the spatial light filter 123.

A portion of the light from the spatial light filer 123 may be reflected towards a part of the second detection system 120-2. The reflective portion of the annular reflector of the spatial light filer 123 may reflect a portion of the collimated measurement light after it has been focused by the third lens 121-3, which is then gathered by a sixth lens 121-6 to form a collimated beam of light. A seventh lens 121-7 may gather the light from the sixth lens 121-7 and focus it onto a prism 113. The prism 113 may split the light into two portions which are detected by a second detector 114-2 and a third detector 114-3. The components 121-3, 123, 121-6, 121-7, 114-2, 114-3, and 113 form the second detection system 120-2. The second detection system 120-2 may be a split detection dark field detection system. The second detection system 120-2 may also be a standard dark field detection system if detectors 114-2, 114-3 and prism 113 are replaced with a single detector. In an embodiment, one or more of the lenses 121 may be replaced with curved mirrors.

The detectors 114 may be a photodiode, photomultiplier tube, a linear detector array, a 2-D detector array, or any other detection system that converts light into an electrical signal. The spatial light filter 123 may be replaced with a window with a small mirror in the middle such the confocal detection system gathers the reflected light and the dark field detection system gathers the transmitted light.

Figure 1F:
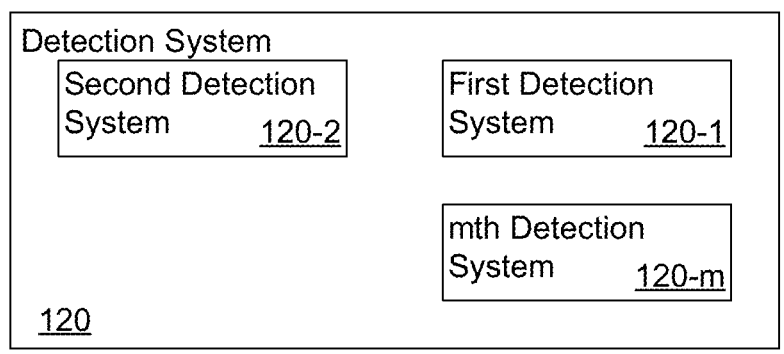
FIG. 1F is a block diagram of a detection system as may be used in an embodiment.

FIG. 1F is an illustration of the detection system 120 in which there are n detection systems including at least a first detection system, a second detection system and an m-th detection wherein n is an integer greater than 2. One of the detection systems 120-$m$ may be an OCT system.

Method 1

Figure 2:
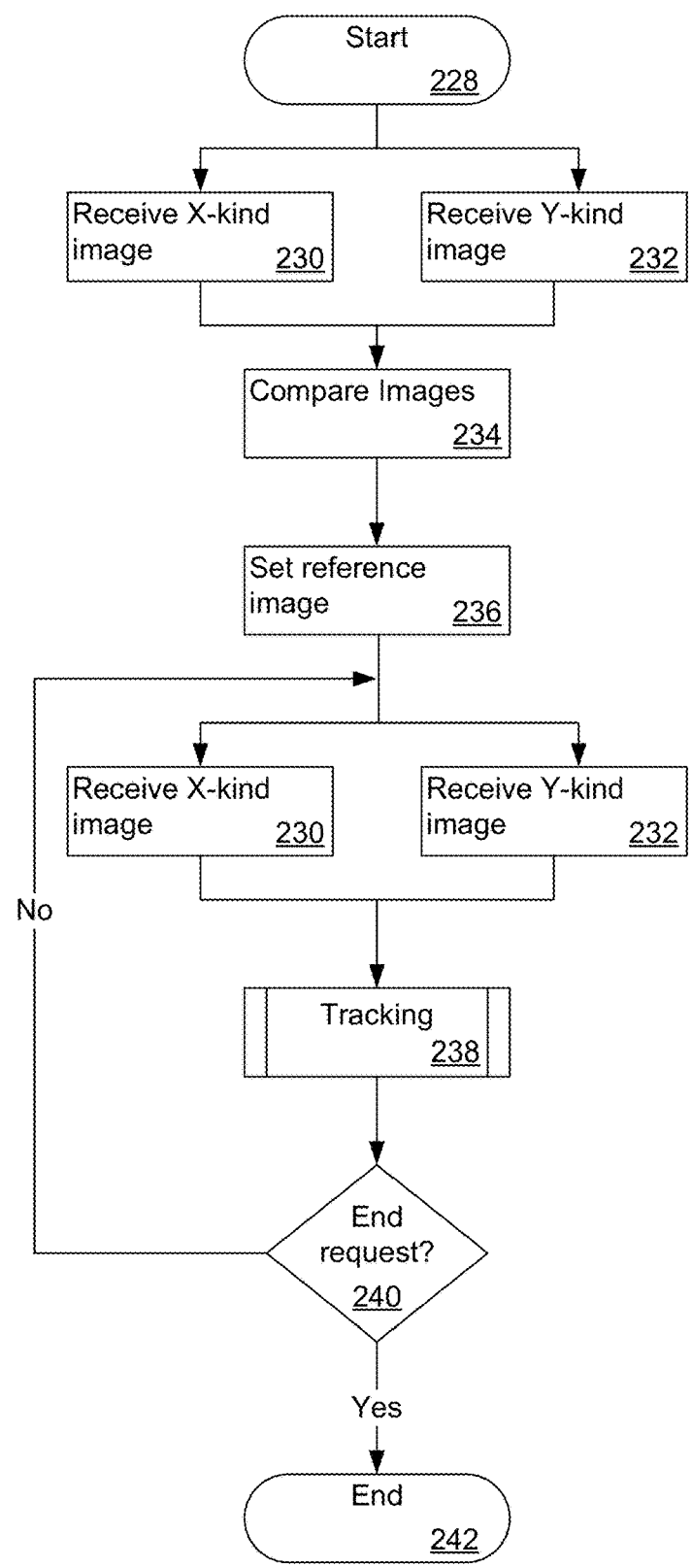
FIG. 2 is an illustration of a method which may be used in an embodiment.

FIG. 2 is an illustration of a method 200 which may be used in an embodiment. The method may be implemented by a controller 116 for an AO-SLO system 100 have at least two kinds of imaging capabilities. An example of the two kinds of imaging capabilities may be a confocal imaging and dark field imaging. A first step in the method 200 may be a step 228 in which the method is started by the controller 116 receiving instructions from an operator to start the method 200. The instructions may be received over a local network, a bus, an internetwork, from a database, from a GUI, or from an electrical switch.

X-kind and Y-kind images are acquired at the same time in steps 230 and 232. In step 230, the controller 116 may receive an X-kind image from the first detection system 120-1 of the imaging apparatus 100. In step 232, the controller 116 may receive a Y-kind image from the second detection system 120-2 of the imaging apparatus 100. The X-kind image and the Y-kind image, may be sent in parallel, in series, or interleaved from the imaging apparatus 100 to the controller 116. The X-kind image and Y-kind image each contain different types of information about the same area of the subject 111 being imaged.

After the controller 116 receives the X-kind image and the Y-kind image the controller 116 may select which of the images is best suited to be set as the reference image in a step 236 with the image selector 116-3. The reference image type may be chosen based upon the contrast ratio, the signal/noise ratio, a histogram, or a combination of this information. The controller 116 may then set the best suited image as a reference image in step 236.

After the reference image has been set, the controller 116 may initiate the image based tracking process. The image based tracking process starts with the controller 116 re-receiving the X-kind image and the Y-kind image in a repeat of steps 230 and 232. The controller 116 may then go onto a tracking process 238 which will be described latter. After the tracking process 238 has finished, the controller 116 may go on to a step 240, in which the controller 116 may determine if the tracking should be stopped. The tracking may be stopped if the controller 116 receives a request from an operator to stop, or if a set series of images has been obtained and tracking is no longer needed. The tracking may also be stopped if an exception occurs, such as if the subject 111 moves away from the imaging apparatus 100 or if the controller 116 receives a signal from the imaging apparatus that there is an issue which indicates that tracking should be stopped. If the tracking is stopped then the method 200 may move on to step 242 in which case a message may be displayed on the display 118. The message may include an image or video produced by the imaging apparatus, data from the imaging apparatus or text message. If the tracking is not stopped the method 200 may move back to steps 230 and 232.

Figure 3:
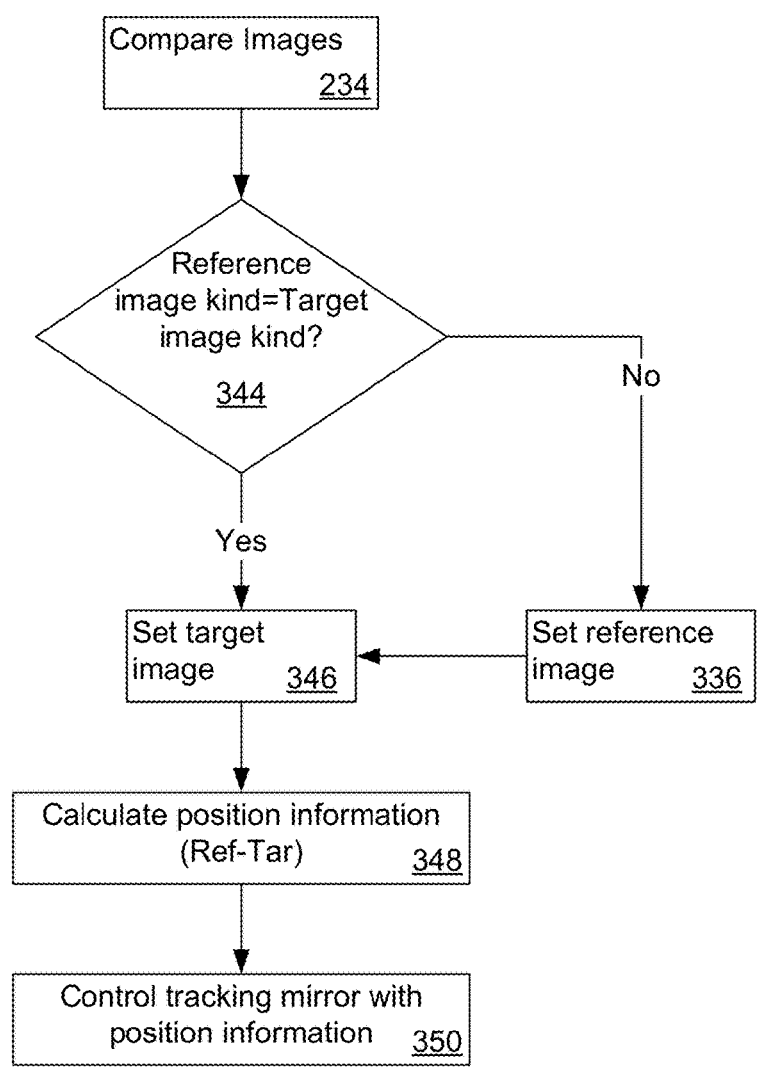
FIG. 3 is an illustration of the tracking method which may be used in an embodiment.

FIG. 3 is an illustration of the tracking method 238 as performed by the controller 116. In a step 234, the newly obtained X-image and Y-image are compared to each other to estimate which is the best image to calculate the position of the subject 111 and should be set as the new target image for tracking purposes. In a step 344, the controller 116 determines if the selected target image's kind (X-image or Y-image) is same as the kind of the most recent reference image. If the selected target image is the same kind as the most recent reference image then the tracking method 238 moves onto a step 346 in which the selected target image is set as the target image. If the selected target image is not the same kind as the most recent reference image then the tracking method 238 moves onto step 336 in which an image which is the same kind as the selected target image is set as the reference image. The image which is set as the new reference image may be the image of the same kind as the selected target image which was taken when the current reference image was obtained or may be a different more recent image of the same kind as the selected target image. The method 238 may move onto the step 346 in which the selected target image is set as the target image by the controller 116.

After the target image has been set, position estimation 116-1 is performed in a step 348. In the step 348, a position of the subject is estimated by using the set reference image and the set target image. The position of the subject 111 may be estimated by comparing entire images, features in the images or regions in the images of the set reference image and the set target image.

In a step 350, the tracking system 116-3 of the controller 116 may calculate a tracking command to be sent to the imaging apparatus 100. The tracking command may be based on the estimated position and the most recent estimated position. The most recent estimated position is the tracking mirror position which was estimated in the most recent cycle of the tracking control system.

The X-kind image and Y-kind image are each obtained with imaging modalities which are different from each other. Examples of such imaging modalities may include but are not limited to: Confocal; Multiple wavelengths; Fluorescence; Non-confocal images; dark field imaging; split detection. An imaging modality may also be a combination of one or more imaging modalities. The image comparison methods used to choose which image is used may include comparing: the cross correlation coefficient between the nearest 2 consecutive images of the same kind; the signal strengths of the acquired images of the different kinds; the signal/noise ratio; the contrast ratio; or the focusing position of the optical system. For example, depending on the depth of focus different images are better for tracking. Combinations of these comparison methods may also be used, such as weighted average of one or more comparison metrics.

Method 2

Figure 4A:
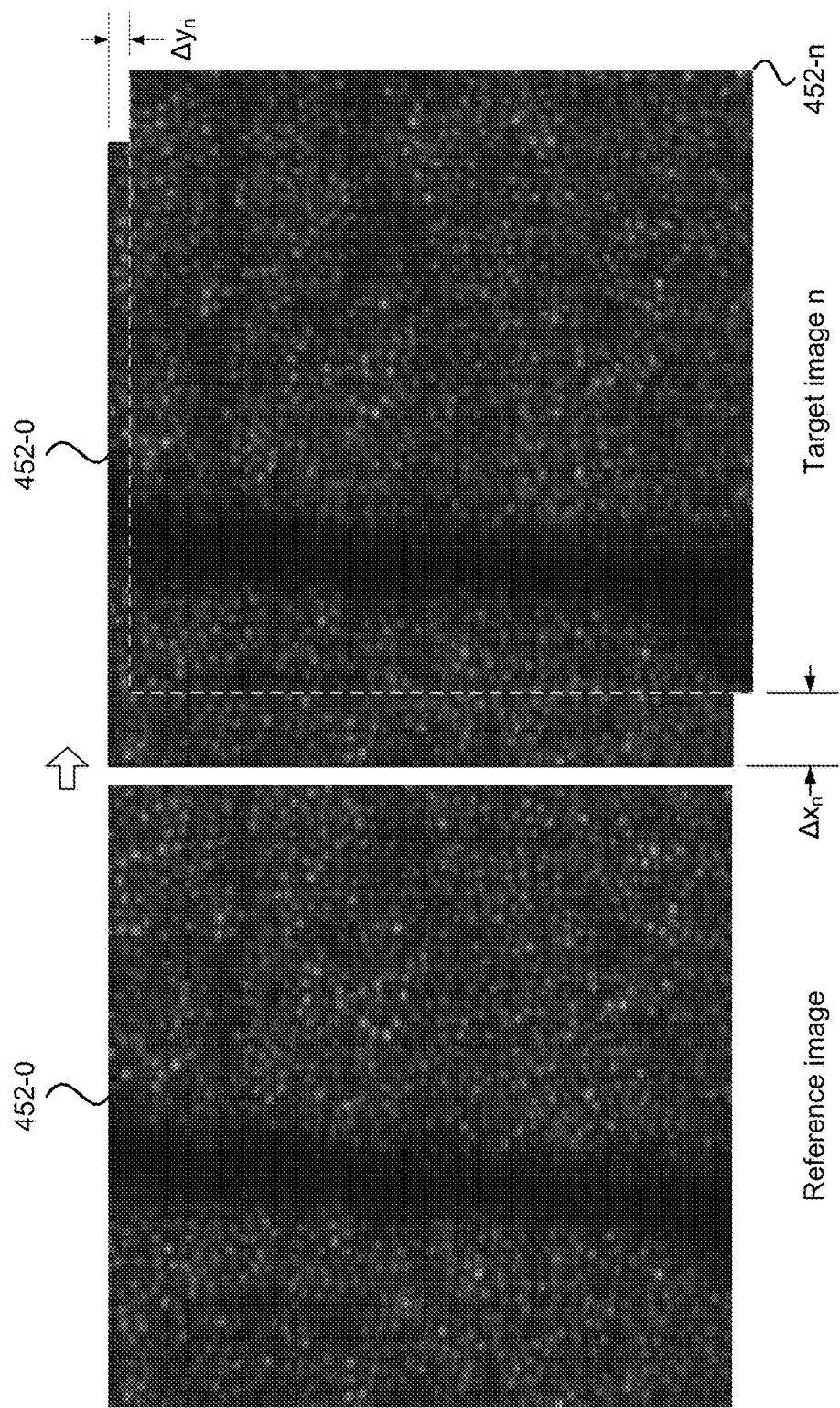
FIGS. 4A-E are illustrations of images of a subject as they may be used in an embodiment.
Figure 4B:
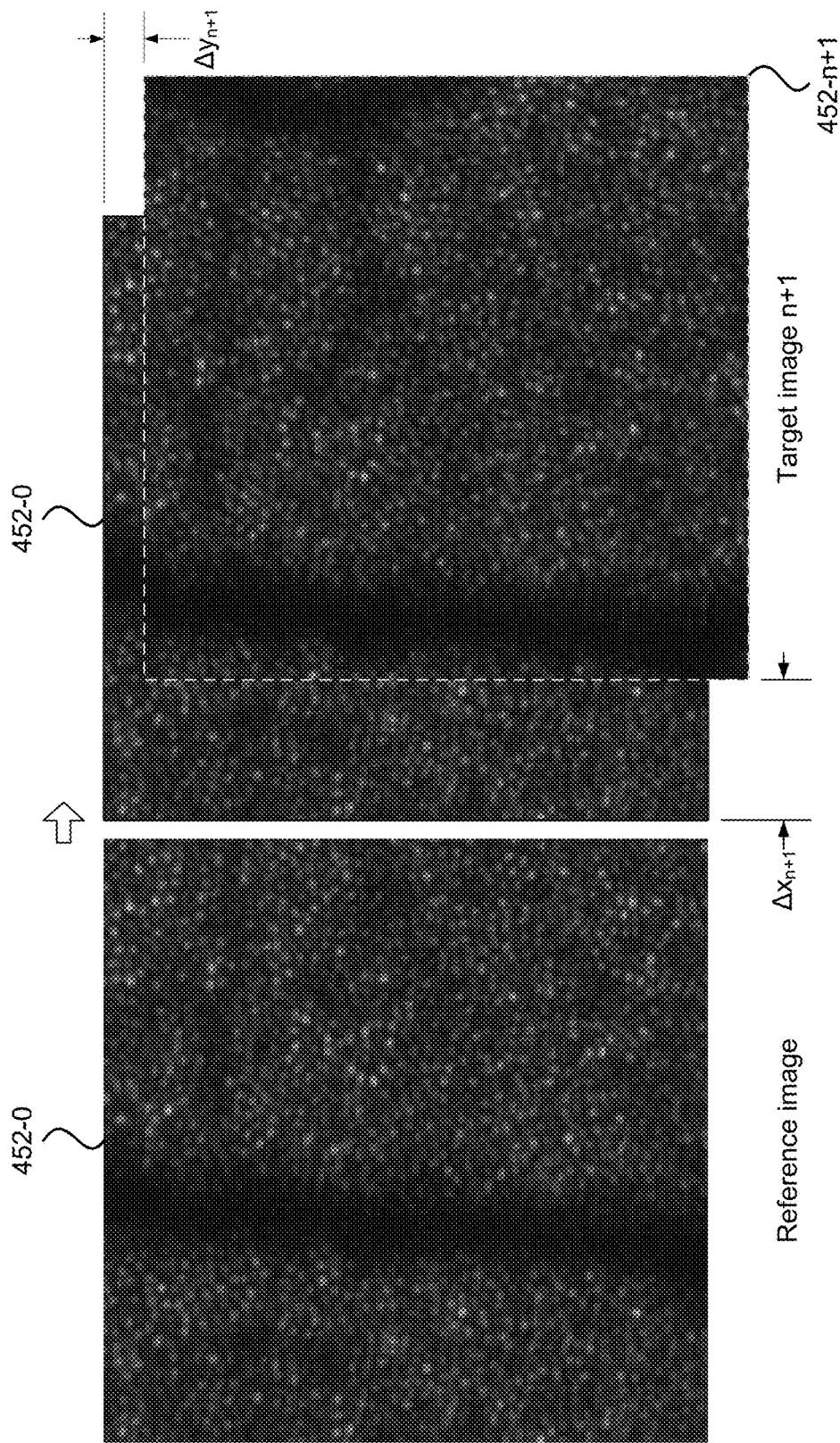

The method described above presumes that the reference image is set at the beginning of imaging. For example, the controller 116 may receive an image from the imaging apparatus 100 or a database. The controller 116 may then set that image as the reference image 452-0, as illustrated in FIG. 4A. The controller 116 may then receive an nth target image 452-$n$ which correlates well with the reference image 452-0 and the controller 116 can estimate $\Delta x_n$ and $\Delta y_n$ based on target image 452-$n$ and reference image 452-0. FIG. 4B illustrates an nth plus one target image 452-$n$+1 which also correlates well with the reference image 452-0 and the controller 116 can estimate $\Delta x_{n+1}$ and $\Delta y_{n+1}$ based on the target image 452-$n$+1 and the reference image 452-0.

As described above the position estimation system 116-1 of the controller 116 may include calculating a cross correlation of a reference image and a target image so as to estimate the relative of position of each image in the context of the subject 111. When the target image n and the target image n+1 have similar image quality, it can be relatively easy to calculate the cross correlation between a fixed reference image and a series of target images.

Figure 4C:
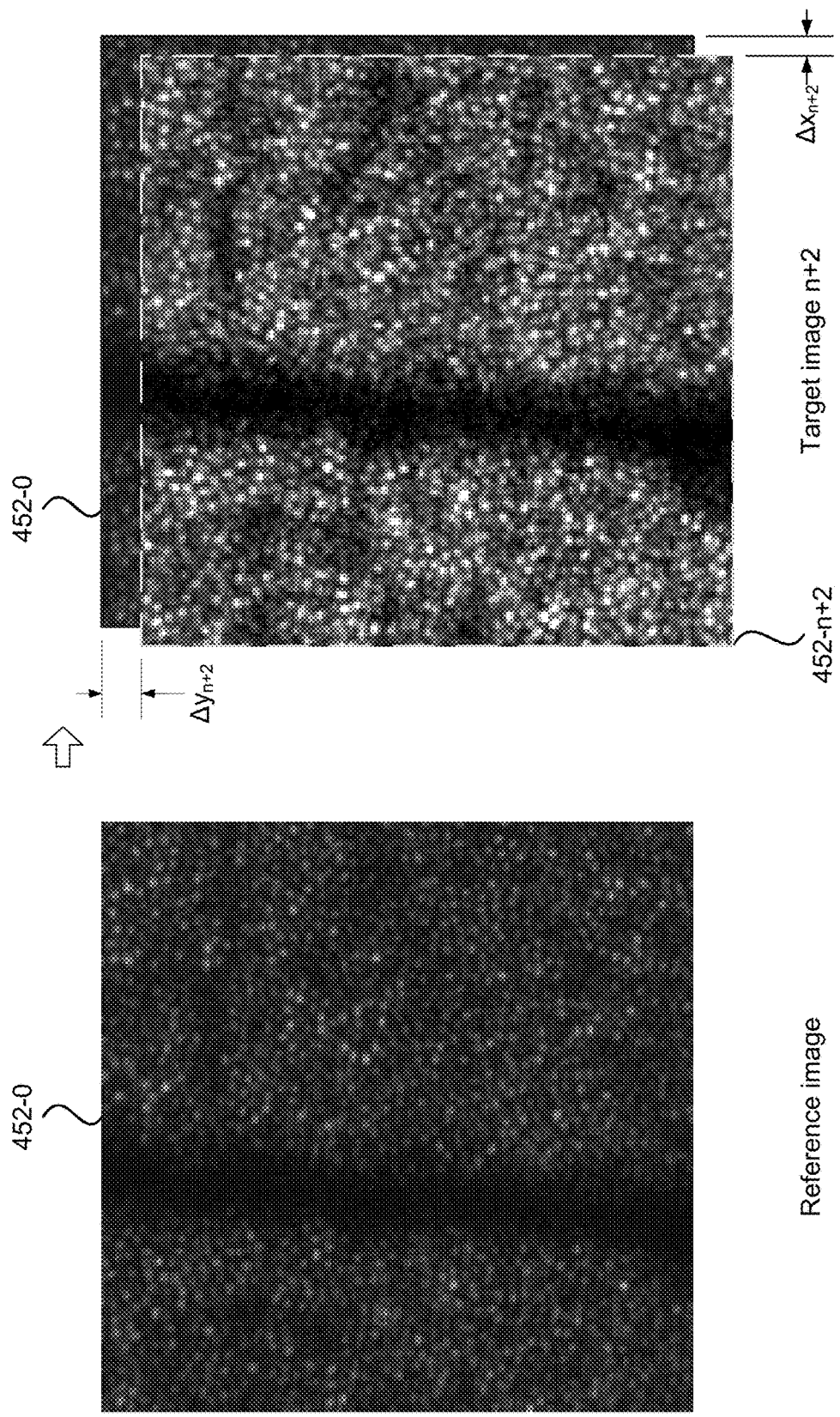
Figure 4D:
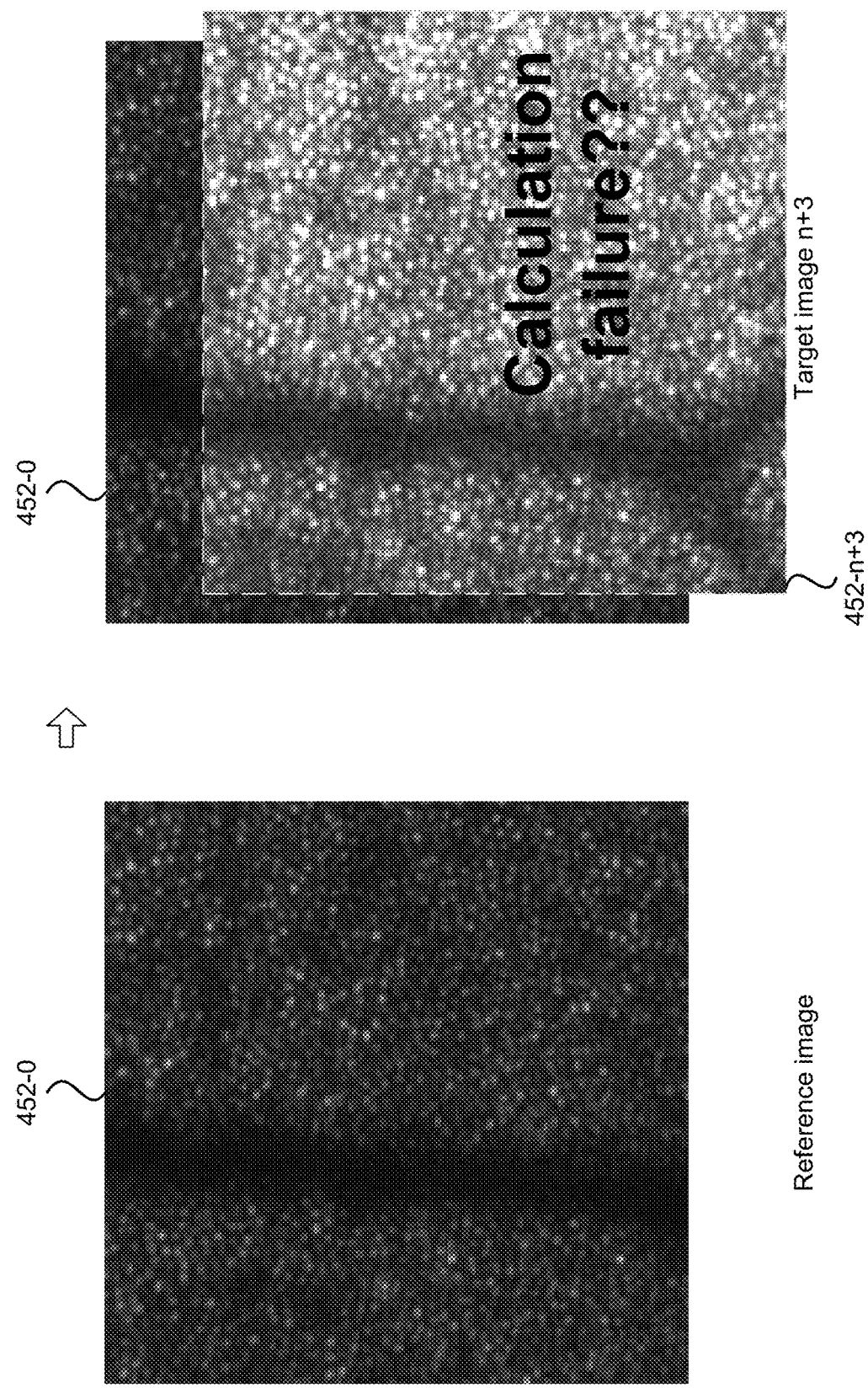

As illustrated in FIG. 4C, the controller 116 may receive a new target image 452-$n$+2, which is qualitatively different from the reference image 452-0 but a good correlation may still be calculated by the controller 116 to obtain a new $\Delta x_{n+2}$ and $\Delta y_{n+2}$. As illustrated in FIG. 4D, the controller 116 may receive a new target image 452-$n$+3 which is qualitatively different from the reference image 452-0 and a good correlation cannot be calculated by the controller 116, which can make it difficult to calculate a reliable new $\Delta x_{n+3}$ and $\Delta y_{n+3}$, in which case tracking may fail or at the very least be delayed. The applicants have come up with a method of addressing this tracking failure.

Figure 4E:
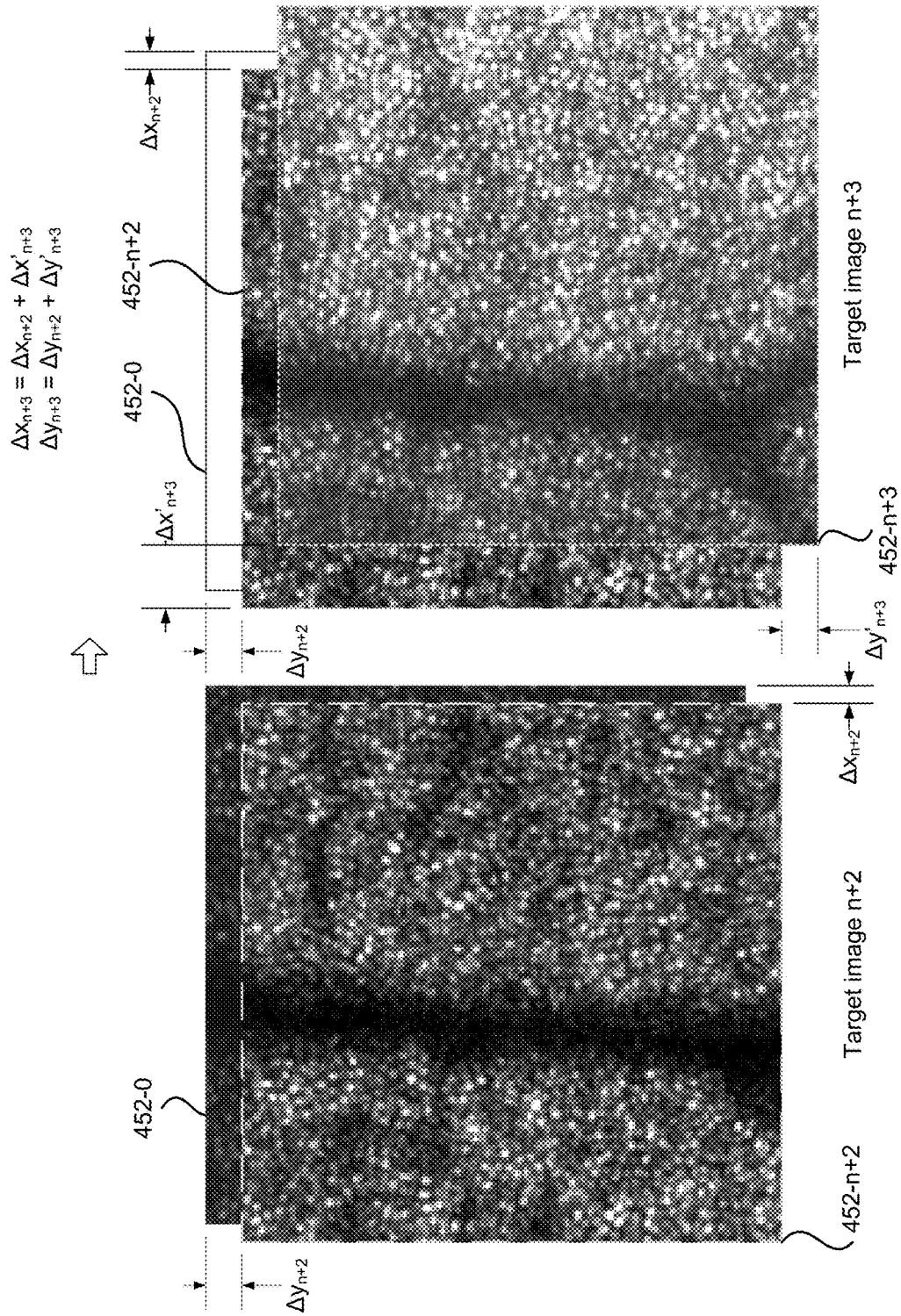

FIG. 4E is an illustration of how the controller 116 obtains $\Delta x_{n+2}$ and $\Delta y_{n+2}$ based on target image 452-$n$+2 and the reference image 452-0. FIG. 4E also illustrates how the controller 116 obtains $\Delta x'_{n+3}$ and $\Delta y'_{n+3}$ based on target image 452-$n$+3 and the target image 452-$n$+3. The offsets $\Delta x'_{n+3}$ and $\Delta y'_{n+3}$ are relative offsets of the new target image relative to a recent target image other than the reference image. The offset relative to the reference image may then be calculated according to equation (1) below.

$$\Delta x_{n+3} = \Delta x_{n+2} + \Delta x'_{n+3}$$

$$\Delta y_{n+3} = \Delta y_{n+2} + \Delta y'_{n+3}$$

$$\vec{\Delta r}_{n+3} = \vec{\Delta r}_{n+2} + \vec{\Delta r'}_{n+3} \qquad (1)$$

Equation (1) essentially describes resetting the reference image to a more recent target image during the imaging session when it is difficult to get a good correlation between the most recent target image and the previous reference image. It is sometimes preferable to calculate relative position between images taken over a shorter period time than images taken over a longer period of time. For example, the reference image which is the basis of the position calculation may be updated if the image kind is changed such as described above or it may be changed based on the image quality or a combination of both.

The applicant has determined that when the target images have some variability in their image quality this has an impact on the ability of the position estimation system 116-1 to determine a relative position of the subject 111. For example, as illustrated in FIG. 4D the image quality of a specific target image 452-$n$+3 may be quite different from the image quality of the reference image 452-0. If the image quality of the target image 452-$n$+3 is too different from the reference image 452-0, the position calculation may be impossible. Which means tracking system may no longer be able to track the movement of the retina.

Figure 5:
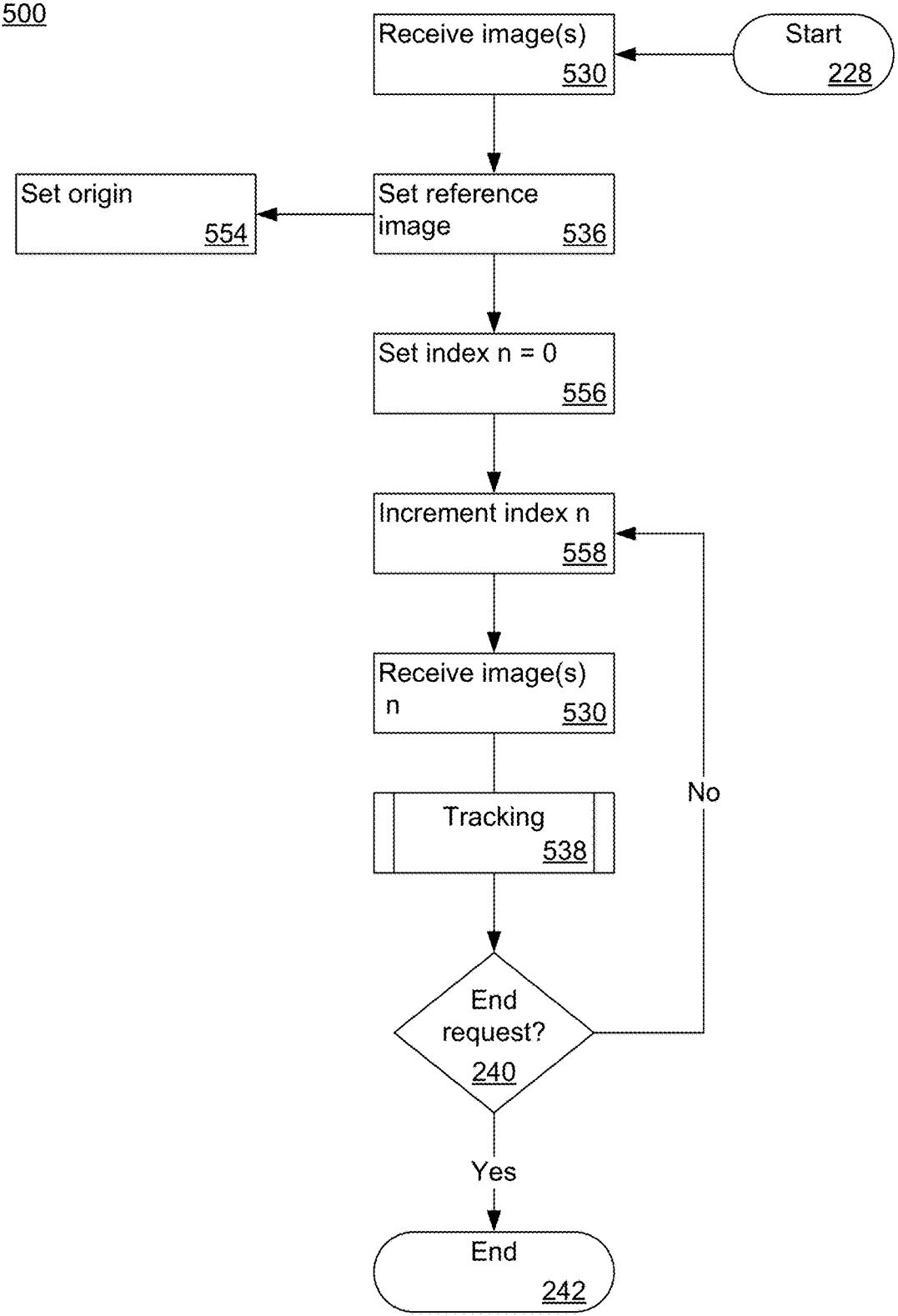
FIG. 5 is an illustration of a method which may be used in an embodiment.

FIG. 5 is an illustration of a method 500 of implementing the reference image resetting system by the controller 116. The method 500 may start with step 228 described above. In a step 530, the controller 116 may receive one or more images as described above in steps 230 and 232 described above. The method 500 is equally applicable to systems that obtain a single image or systems that obtain multiple images in parallel. The method 500 may include the step 234 or its equivalent.

In a step 536, the controller 116 chooses an image as the reference image 452-0. The chosen reference image 452-0 may be a recently obtained image or a previously saved image retrieved from a non-transitory computer readable storage medium. While setting the reference image the controller 116 may also set the origin in a step 554. The index n may then be set to zero in a step 556. After which the index n may be incremented in a step 558. The controller 116 may then move onto a repeat of step 530 except these images are tagged with the index n. The tracking sub-method 538 which will be described later may be called after step 530. The controller 116 may go on to a step 240, described above in which the controller 116 may determine if the tracking should be stopped. If the tracking is stopped then the method 500 may move on to a step 242, described above. If the tracking is not stopped then the method 500 may move back to step 558.

Figure 6:
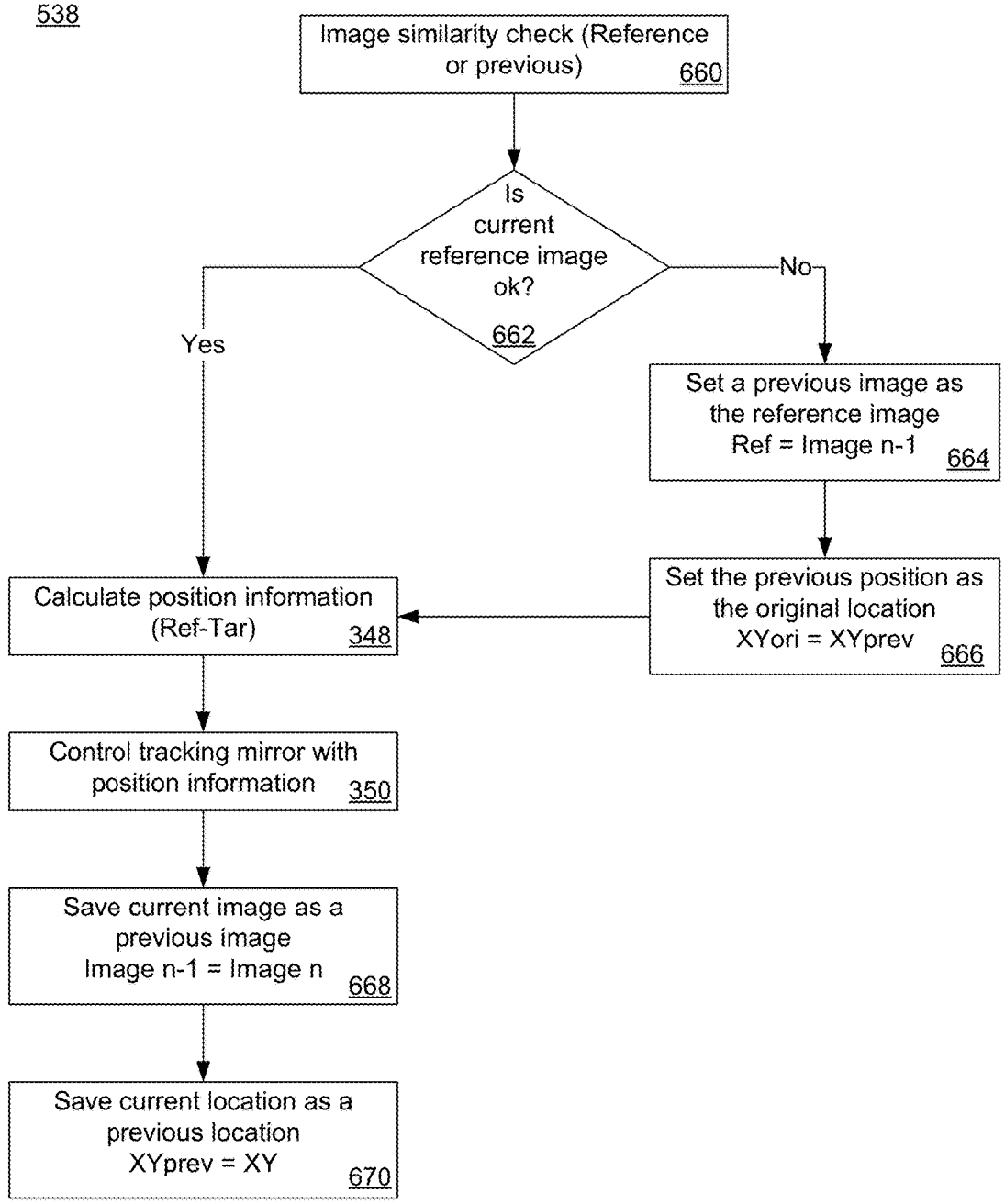
FIG. 6 is an illustration of a method which may be used in an embodiment.

FIG. 6 is an illustration of the tracking sub-method 538 as may be implemented by the controller 116 in an embodiment. The tracking sub-method 538 may be combined with the tracking sub-method 238. The tracking sub-method 538 may include a step 660 in which the similarity of the current target image 452-n is checked against the current reference image 452-0 by the controller 116. The similarity of the new target image and the reference image may be calculated based on one or more of: a pixel value average of the images; a distribution (histogram) of pixel value of the images; a cross correlation coefficient of the images; and a cross correlation coefficient of limited center portion of the images. In a step 662, the controller 116 may determine if the current reference image is ok. If the answer is yes, then the sub-method 538 may go on to step 348. If the answer is no then the sub-method 538 may go on to step 664, in which a previous image is set as the reference image. The criteria for checking the similarity can be set automatically or manually. If the similarity check uses pixel average, a difference of 25% may be acceptable. If the similarity check uses cross correlation of the images, then a threshold of over 0.5 for a peak correlation coefficient may be acceptable. In one embodiment, the most recent target image 452-n−1 is set as a new reference image 452-0. Then in a step 666, an origin (XYori) is set as the position of the previous image that was set as the target image. After the origin is set the sub-method 538 go on to step 348.

In the step 348 a position of the subject is estimated by using the set reference image and the set target image as described above. Then in a step 350, the tracking system 116-3 of the controller 116 may calculate a tracking command to be sent to the imaging apparatus 100 as described above. After which in a step 668 the current image may be saved as a previous image that might be used later in a future step 664. In a step 670 the current location (XY) which is determined in step 348 is saved as previous position XYprev and may be used in a future step 666.

If the image quality or image kind changes during an imaging session, the reference image 452-0 which is compared to target images may be updated by the method describe above. The target image n+1 may be relatively similar to the target image n, so the reference image is exchanged to the target image n instead of the original reference image. A cross-correlation method may be used to estimate the relative position between the target image n and a previous image n−1. The relative position of an image n relative the most recent image n−1 may be defined as $\vec{\Delta r'}_n$. While an absolute position $\vec{\Delta r}_n$ may be defined relative to the original origin. Equation (2) below may describe the relationship between the two. Wherein $\vec{\Delta r}_{n-1}$ is the absolute position of the most recent previous image relative to the original origin.

$$\vec{\Delta r}_n = \vec{\Delta r}_{n-1} + \vec{\Delta r'}_n \quad (2)$$

Equation (2) may also be generalized to equation (3) which applies to situations in which a previous image at an index i is used instead of the most recent image. For an image n there is a vector $\vec{\Delta r}_{n,i}$ which represents the relative position of an image n to a new reference image i. In which i is an integer between 0 and n−1. When i is zero then the new reference image is referencing the original reference image.

$$\vec{\Delta r}_{n,0} = \vec{\Delta r}_{i,0} + \vec{\Delta r}_{n,i} \quad (3)$$

Examples of Images Obtained with an Embodiment

Figure 7A:
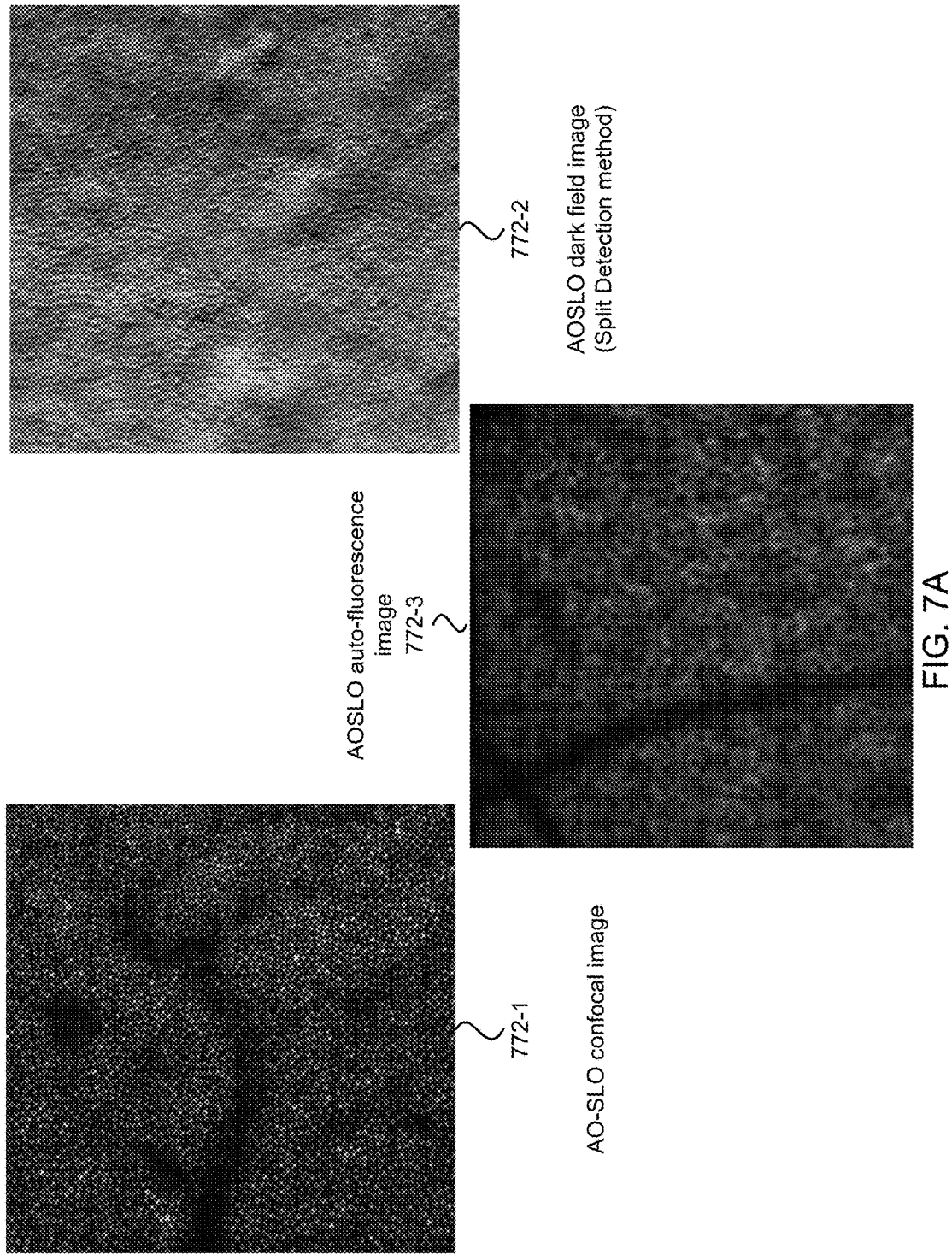
FIGS. 7A-D are illustrations of images obtained from a subject by an embodiment.

FIG. 7A is an illustration of three different kinds of images that may be obtained by an embodiment at the same location using an AO-SLO that is capable of obtaining different kinds of images of the same area of the fundus. Image 772-1 is an example of an AO-SLO confocal image taken with confocal detection system such as first detection system 120-1. Image 772-2 is an example of an AO-SLO dark field image taken with second detection system 120-2. Image 772-3 is an example of AO-SLO auto-fluorescence image taken with a third detection system 120-3.

Figure 7B:
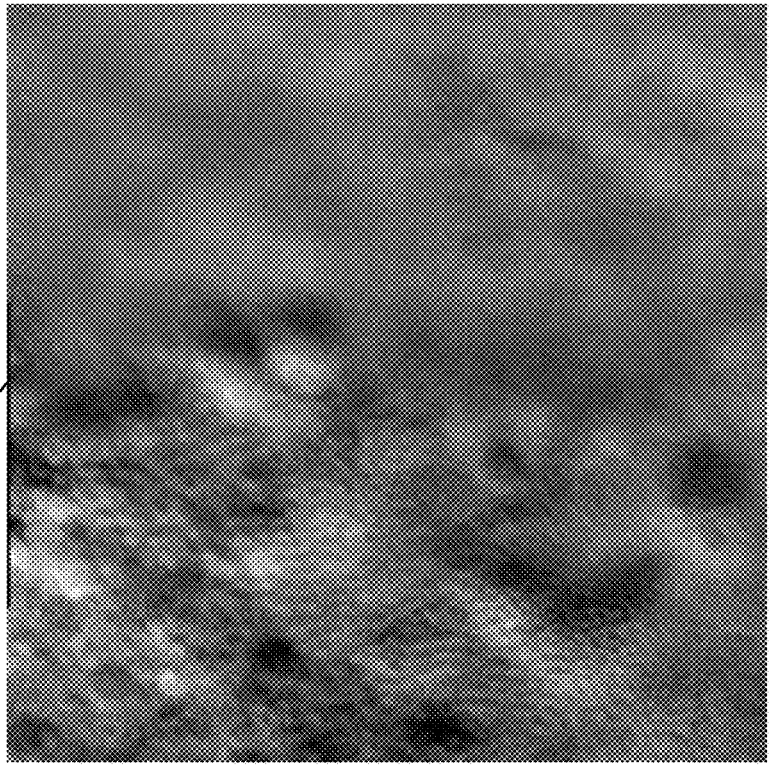
Figure 7B:
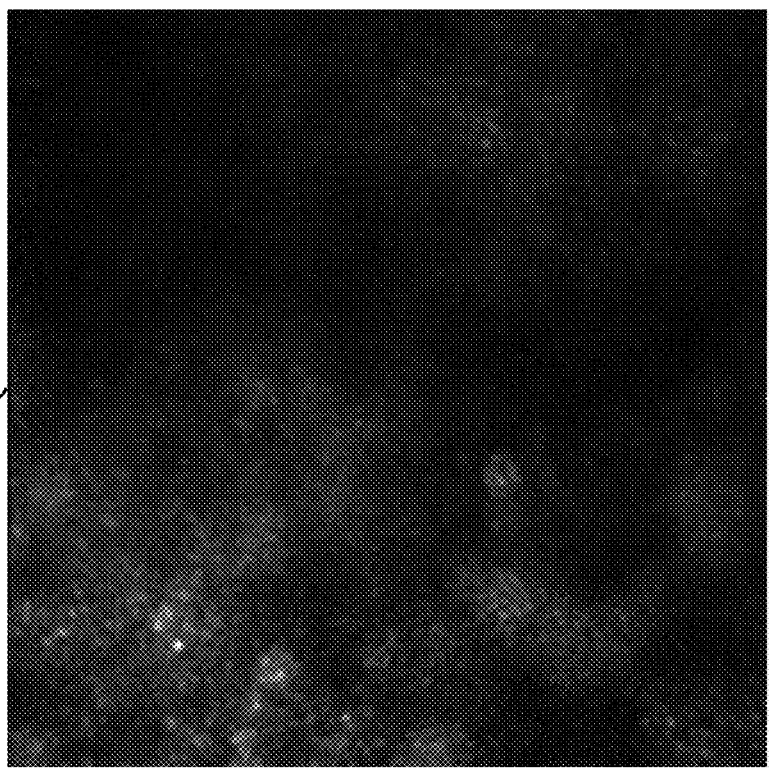

FIG. 7B is an illustration of two different kinds of images that may be obtained by an embodiment at the same location of a diseased eye using an AO-SLO that is capable of obtaining different kinds of images of the same area of the fundus. Image 774-1 is an example of an AO-SLO confocal image taken with confocal detection system such as first detection system 120-1. Image 774-2 is an example of an AO-SLO dark field image taken with second detection system 120-2.

Figure 7C:
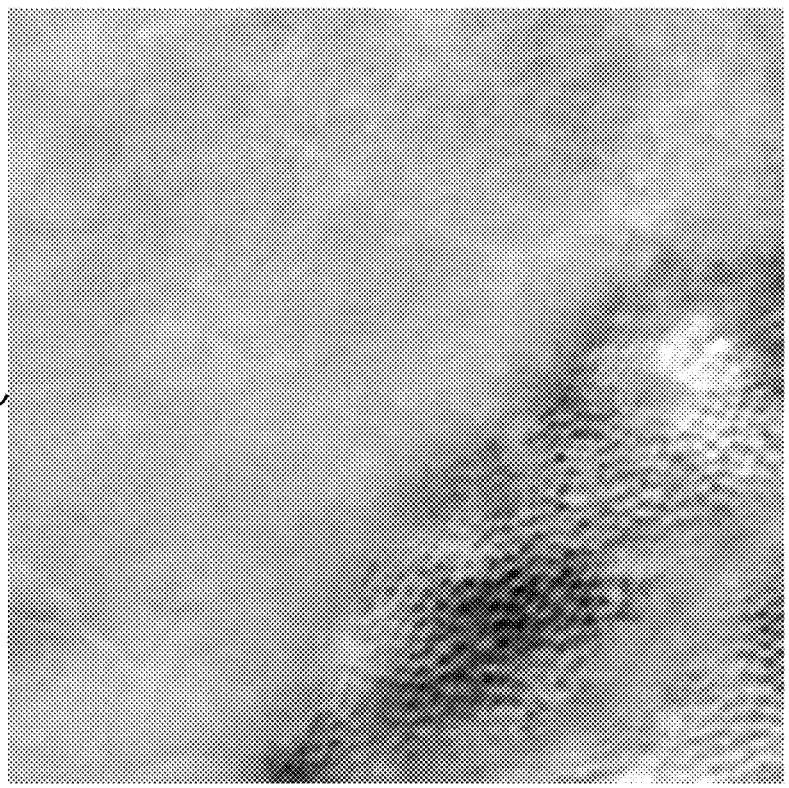
Figure 7C:
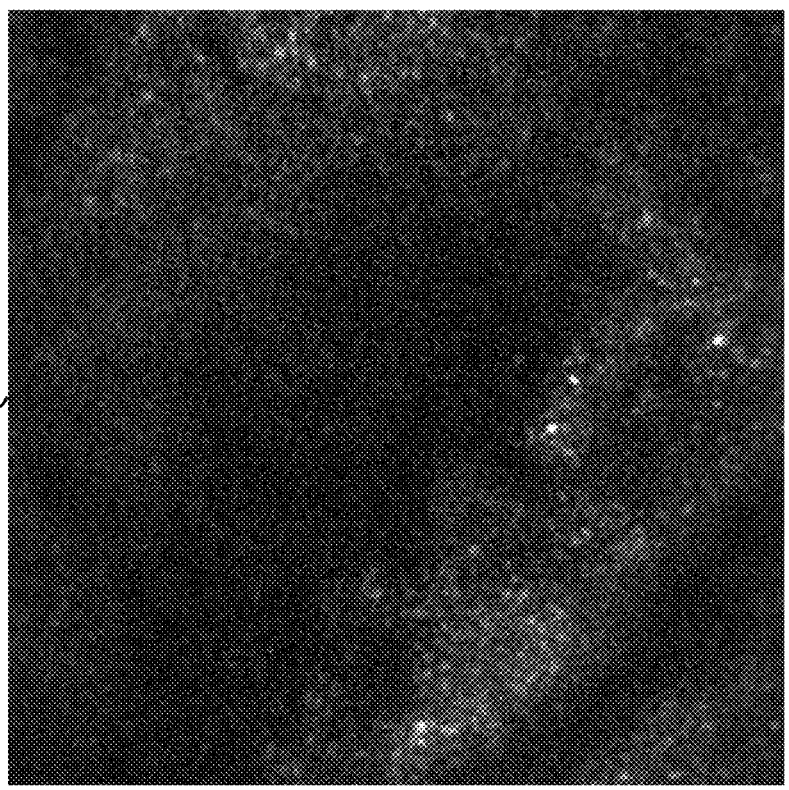

FIG. 7C is an illustration of two different kinds of images that may be obtained by an embodiment at the same location of a diseased eye using an AO-SLO that is capable of obtaining different kinds of images of the same area of the fundus. Image 776-1 is an example of an AO-SLO confocal image taken with confocal detection system such as the first detection system 120-1. Image 776-2 is an example of an AO-SLO dark field image taken with second detection system 120-2.

Figure 7D:
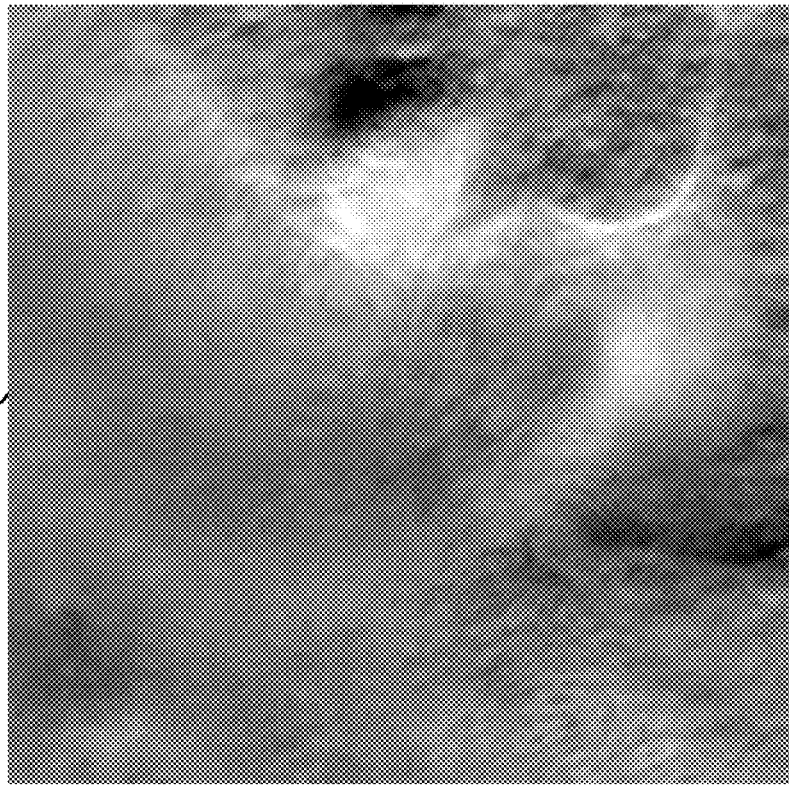
Figure 7D:
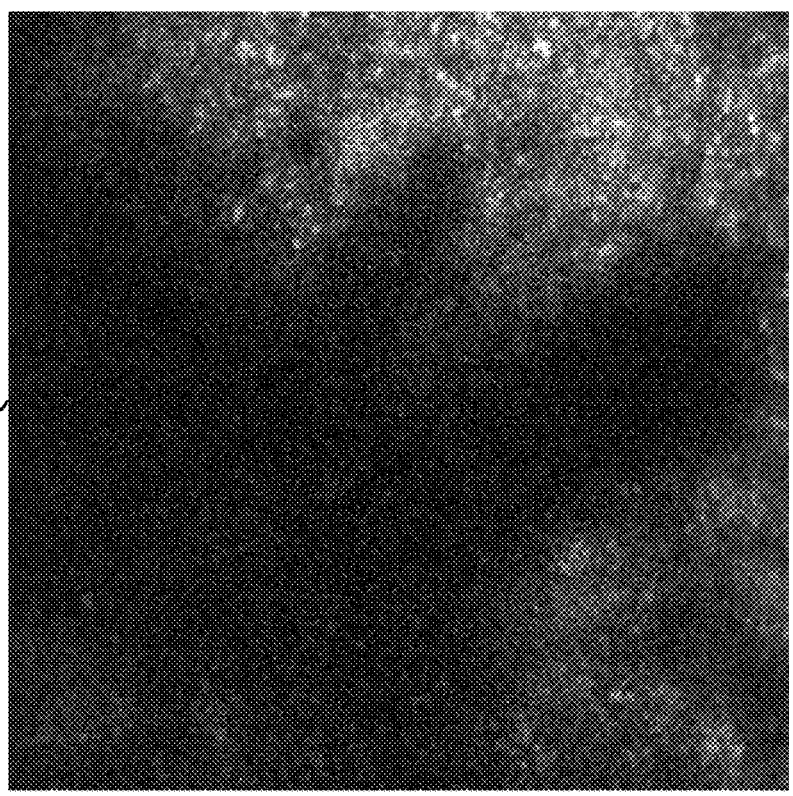

FIG. 7D is an illustration of two different kinds of images that may be obtained by an embodiment at the same location of a diseased eye using an AO-SLO that is capable of obtaining different kinds of images of the same area of the fundus. Image 778-1 is an example of an AO-SLO confocal image taken with confocal detection system such as the first detection system 120-1. Image 778-2 is an example of an AO-SLO dark field image taken with second detection system 120-2.

Figure 8:
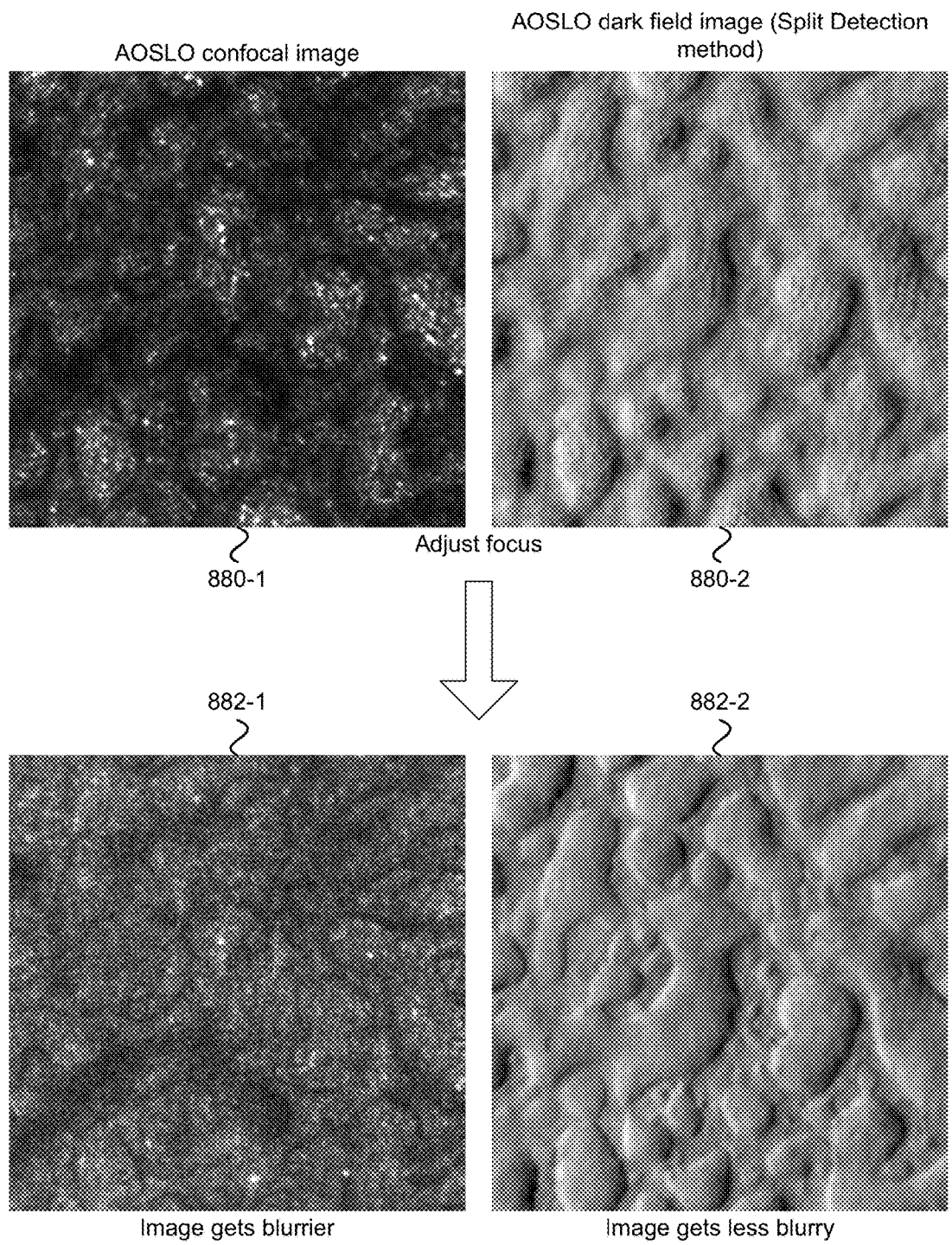
FIG. 8 is an illustration of images obtained from a subject by an embodiment.

FIG. 8 is an illustration of two different kinds of images that may be obtained by an embodiment at the same location of a subject 111 using an AO-SLO 100 that is capable of obtaining different kinds of images of the same area of the fundus. Image 880-1 is an example of an AO-SLO confocal image taken with confocal detection system such as the first detection system 120-1. Image 880-2 is an example of an AO-SLO dark field image taken with second detection system 120-2. Note that image 880-1 appears to be more in focus then image 880-2. If the focus is adjusted then confocal image 882-1 and dark field image 882-2 are obtained. Please note that after the focus is adjusted the confocal image gets blurrier while the dark filed image gets less blurry. Which image is in focus may effect which image is used for tracking in an embodiment.

Figure 9:
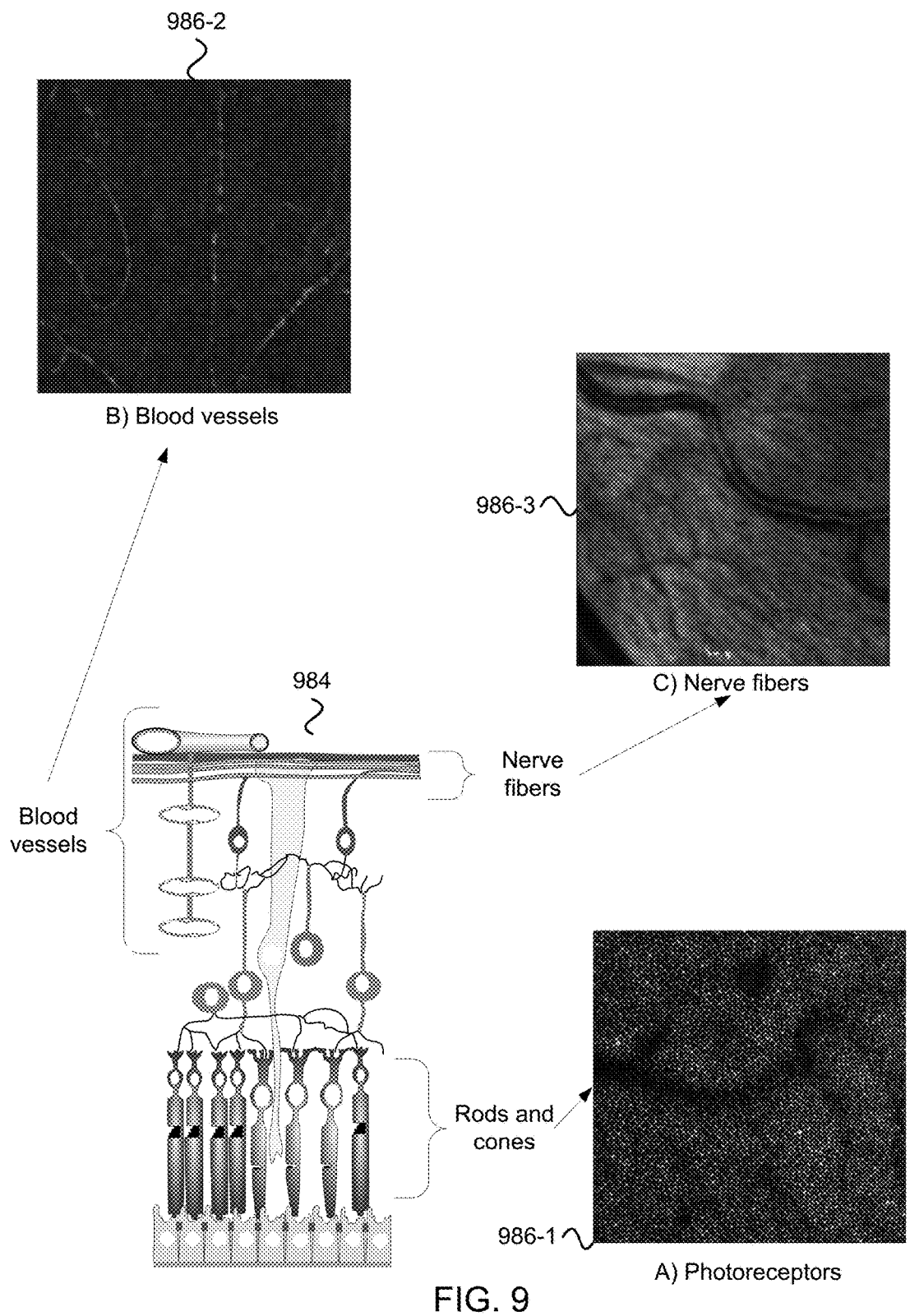
FIG. 9 is an illustration of images obtained from a subject by an embodiment.

FIG. 9 includes a diagram 984 illustrating a cross section of the different portions of the subject 111. An embodiment may obtain different images of different cross sections of the same area of the subject such as image 986-1 of the photoreceptors, image 986-2 of the blood vessels, and image 986-3 of the nerve fibers. Each of the images 986-1, 986-2, and 986-3 may be different kind of images and the image tracking system may switch between the different kinds of images during an imaging session.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. A method of controlling an ophthalmic apparatus to produce images of an area of an eye, wherein the apparatus scans the area with light, divides return light from the area into a first portion of light and a second portion of light, receives the first potion of the return light and the second portion of the return light with a first detection unit and a second detection unit respectively, generates a first image of the area based on the received first portion of the return light, and generates a second image of the area based on the received second portion of the return light, the method comprising:
receiving the first image and the second image;
comparing the first image and the second image;
selecting the first image or the second image based on a result of the comparing step as a position detection image; and
estimating a change in position of the area based on the selected position detection image.

2. The method according to claim 1 further comprising sending instructions to the apparatus to adjust the area based on the estimated change in position of the area.

3. The method according to claim 1, wherein:
the first portion of the return light has a first range of wavelengths;
the second portion of the return light has a second range of wavelengths; and
the first range of wavelengths is different from the second range of wavelengths.

4. The method according to claim 1, wherein
the first portion of the return light is fluorescence light; and
the second portion of the return light is not fluorescence light.

5. The method according to claim 1, wherein
the first portion of the return light passes through a confocal pinhole before being detected by a first detector to generate the first image; and
the second portion of the return light does not pass through the confocal pinhole before being detected by a second detector to generate the second image.

6. The method according to claim 1, wherein selecting the first image or the second image as the position detection image comprises:
estimating a first cross correlation value based on the first image and a previous first image;
estimating a second cross correlation value based on the second image and a previous second image;
selecting the first image as the position detection image if the first cross correlation value is greater than the second cross correlation value; and
selecting the second image as the position detection image if the second cross correlation value is greater than the first cross correlation value.

7. The method according to claim 1, wherein selecting the first image or the second image as the position detection image comprises:
selecting the first image as the position detection image if average signal strength of the first image is greater than average signal strength of the second image; and
selecting the second image as the position detection image if the average signal strength of the second image is greater than the average signal strength of the first image.

8. The method according to claim 1, wherein selecting the first image or the second image as the position detection image comprises:
estimating a first difference based on a difference between a focus position of the first image and a set focus position;
estimating a second difference based on a difference between a focus position of the second image and the set focus position; and
selecting the first image as the position detection image if the first difference is less than the second difference.

9. The method according to claim 1, wherein the position detection image is set as a reference image which is used as a point of comparison for image tracking in subsequent position tracking during a second period of time after a first period of time,
wherein the first period of time and the second period of time are same time for one scan of the area.

10. The method according to claim 9, further comprising replacing the reference image with a new reference image.

11. The method according claim 10, wherein replacing the reference image with the new reference image further comprises:
selecting the new reference image from a plurality of images.

12. The method according to claim 11, wherein the new reference image is selected based on average intensity of each of the plurality of images.

13. The method according to claim 11 wherein the new reference image is selected based on a distribution of intensity of pixels within each of the plurality of images.

14. The method according to claim 11, wherein the new reference image is selected based on cross correlation coefficients calculated among the plurality of images.

15. The method according to claim 10, wherein the new reference image is constructed from an average of the plurality of images.

16. A controller that is configured to control an ophthalmic apparatus to produce images of an area of an eye, wherein the apparatus scans the area with light, divides return light from the area into a first portion of light and a second portion of light, receives the first potion of the return light and the second portion of the return light with a first detection unit and a second detection unit respectively, generates a first image of the area based on the received first portion of the return light, and generates a second image of the area based on the received second portion of the return light, the controller comprising:
a processor; and
a memory;
wherein the processor receives the first image and the second image;
wherein the processor compares the first image and the second image;
wherein the processor selects the first image or the second image based on the comparing result as a position detection image; and
wherein the processor estimates a change in position of the area based on the selected position detection image.

17. The controller according to claim 16, further comprising the ophthalmic apparatus.

18. The ophthalmic of claim 17 further comprising:
one or more light sources to provide the light with which the area is scanned; and
a scanner for scanning the area with the light.

19. A non-transitory computer readable storage medium encoded with instructions for performing a method of controlling an ophthalmic apparatus to produce images of an area of an eye, wherein the apparatus scans the area with light, divides return light from the area into a first portion of light and a second portion of light, receives the first potion of the return light and the second portion of the return light with a first detection unit and a second detection unit respectively, generates a first image of the area based on the received first portion of the return light, and generates a second image of the area based on the received second portion of the return light, the instructions comprising:
instructions for receiving the first image and the second image;
instructions for comparing the first image and the second image;
instructions for selecting the first image or the second image based on the compared result as a position detection image; and
instructions for estimating a change in position of the area based on the selected position detection image.

* * * * *